(12) United States Patent
Ono

(10) Patent No.: US 12,582,311 B2
(45) Date of Patent: Mar. 24, 2026

(54) OPHTHALMIC APPARATUS

(71) Applicant: Topcon Corporation, Tokyo (JP)

(72) Inventor: Yusuke Ono, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 931 days.

(21) Appl. No.: 17/774,486

(22) PCT Filed: Dec. 21, 2020

(86) PCT No.: PCT/JP2020/047608
§ 371 (c)(1),
(2) Date: May 5, 2022

(87) PCT Pub. No.: WO2021/153087
PCT Pub. Date: Aug. 5, 2021

(65) Prior Publication Data
US 2022/0386868 A1 Dec. 8, 2022

(30) Foreign Application Priority Data

Jan. 30, 2020 (JP) ................................. 2020-013120

(51) Int. Cl.
*A61B 3/117* (2006.01)
*A61B 3/00* (2006.01)
(Continued)

(52) U.S. Cl.
CPC ............ *A61B 3/117* (2013.01); *A61B 3/0025* (2013.01); *A61B 3/102* (2013.01); *A61B 3/12* (2013.01)

(58) Field of Classification Search
CPC ....... A61B 3/0025; A61B 3/102; A61B 3/107; A61B 3/117; A61B 3/12
See application file for complete search history.

(56) References Cited

U.S. PATENT DOCUMENTS

2012/0140174 A1 6/2012 Hee et al.
2013/0003074 A1 1/2013 Kurosaka
(Continued)

FOREIGN PATENT DOCUMENTS

JP 2011-147611 A 8/2011
JP 2013-226383 A 11/2013
(Continued)

OTHER PUBLICATIONS

International Search Report and Written Opinion mailed on Feb. 2, 2021, received for PCT Application PCT/JP2020/047608, Filed on Dec. 21, 2020, 10 pages including English Translation.
(Continued)

*Primary Examiner* — Jack Dinh
(74) *Attorney, Agent, or Firm* — XSENSUS LLP

(57) ABSTRACT

In the ophthalmic apparatus 1 of an aspect example, the image acquiring unit (the fundus camera unit 2, the OCT unit 100, the image data constructing unit 220) acquires an anterior segment image constructed based on data collected from an anterior segment of a subject's eye by OCT scanning. The part image identifying processor 231 performs identification of two or more part images respectively corresponding to two or more parts of the anterior segment from the anterior segment image acquired. The part image assessing processor 232 performs image quality assessment of each of the two or more part images. The anterior segment image assessing processor 233 performs image quality assessment of the anterior segment image based on two or more pieces of assessment data respectively obtained for the two or more part images.

9 Claims, 19 Drawing Sheets

(51) Int. Cl.
    *A61B 3/10*         (2006.01)
    *A61B 3/12*         (2006.01)

(56)            References Cited

U.S. PATENT DOCUMENTS

| | | |
|---|---|---|
| 2013/0258280 A1 | 10/2013 | Goto |
| 2013/0301008 A1 | 11/2013 | Srivastava et al. |
| 2015/0085252 A1 | 3/2015 | Fujimura et al. |
| 2015/0092160 A1 | 4/2015 | Chen et al. |
| 2015/0245765 A1 | 9/2015 | Fujii et al. |
| 2016/0089020 A1 | 3/2016 | Gomi et al. |
| 2016/0317012 A1 | 11/2016 | Bagherinia |
| 2016/0317029 A1 | 11/2016 | Srivastava et al. |
| 2016/0345822 A1 | 12/2016 | Fujimura et al. |
| 2021/0161376 A1 | 6/2021 | Ono |

FOREIGN PATENT DOCUMENTS

| | | |
|---|---|---|
| JP | 2013-248376 A | 12/2013 |
| JP | 2014-500096 A | 1/2014 |
| JP | 2015-43814 A | 3/2015 |
| JP | 2015-66083 A | 4/2015 |
| JP | 2015-515894 A | 6/2015 |
| JP | 2015-160103 A | 9/2015 |
| JP | 6023406 B2 | 11/2016 |
| JP | 2018-102789 A | 7/2018 |
| JP | 2019-088382 A | 6/2019 |
| JP | 2019-213740 A | 12/2019 |
| WO | 2014/192520 A1 | 12/2014 |
| WO | 2014/203901 A1 | 12/2014 |

OTHER PUBLICATIONS

Japanese Office Action issued Dec. 5, 2023, in corresponding Japanese Patent Application No. 2020-013120, 10 pages.
Extended European Search Report issued Dec. 22, 2023, in corresponding European Patent Application No. 20916257.7, 9 pages.
Office Action issued on Apr. 9, 2024, in corresponding Japanese patent Application No. 2020-013120, 6 pages.

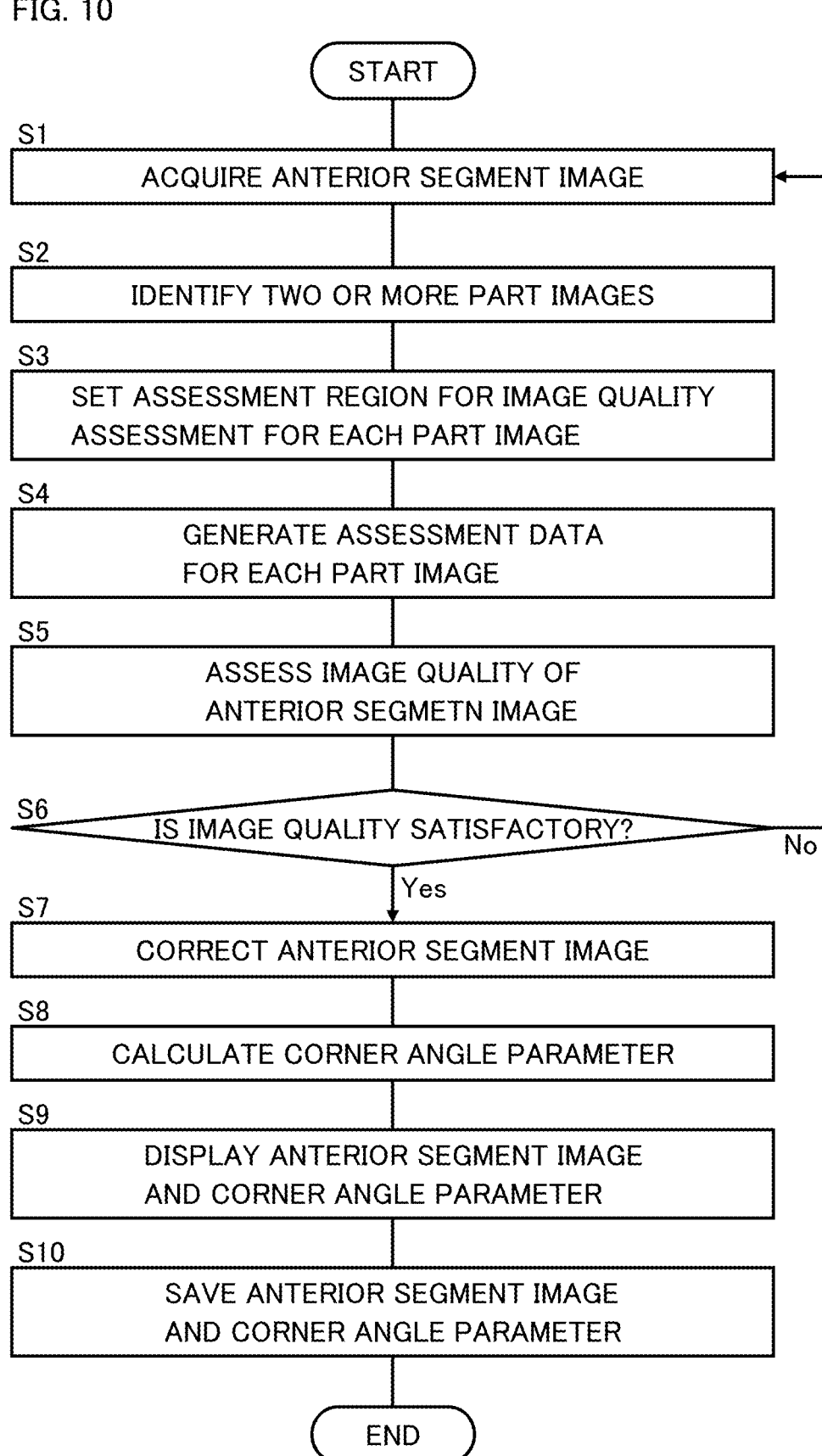

START

S1
ACQUIRE ANTERIOR SEGMENT IMAGE

S2
IDENTIFY TWO OR MORE PART IMAGES

S3
SET ASSESSMENT REGION FOR IMAGE QUALITY
ASSESSMENT FOR EACH PART IMAGE

S4
GENERATE ASSESSMENT DATA
FOR EACH PART IMAGE

S5
ASSESS IMAGE QUALITY OF
ANTERIOR SEGMETN IMAGE

S6
IS IMAGE QUALITY SATISFACTORY?
No
Yes

S7
CORRECT ANTERIOR SEGMENT IMAGE

S8
CALCULATE CORNER ANGLE PARAMETER

S9
DISPLAY ANTERIOR SEGMENT IMAGE
AND CORNER ANGLE PARAMETER

S10
SAVE ANTERIOR SEGMENT IMAGE
AND CORNER ANGLE PARAMETER

END

FIG. 12

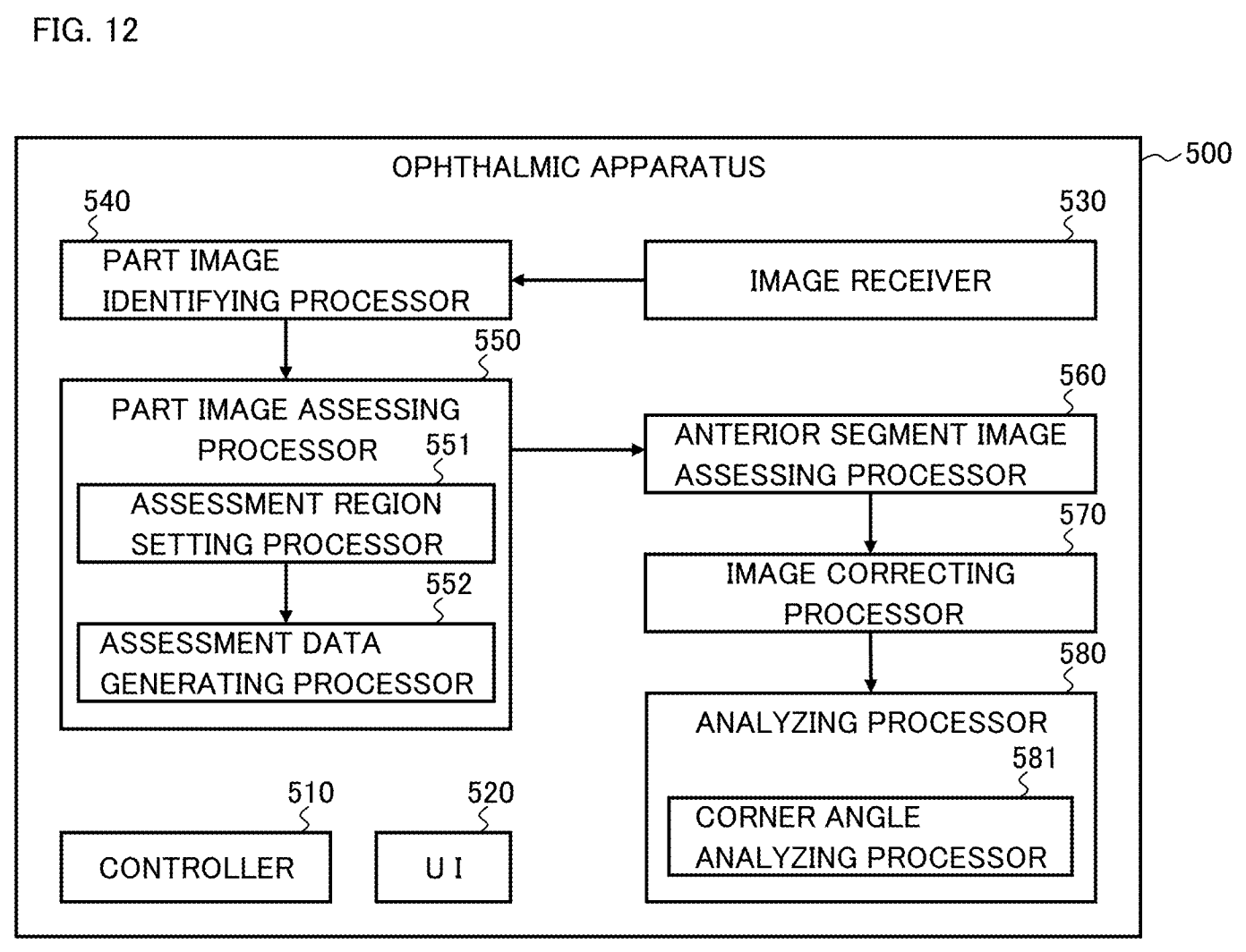

OPHTHALMIC APPARATUS 500

IMAGE RECEIVER 530

ANTERIOR SEGMENT IMAGE ASSESSING PROCESSOR 560

IMAGE CORRECTING PROCESSOR 570

ANALYZING PROCESSOR 580

CORNER ANGLE ANALYZING PROCESSOR 581

PART IMAGE IDENTIFYING PROCESSOR 540

PART IMAGE ASSESSING PROCESSOR 550

ASSESSMENT REGION SETTING PROCESSOR 551

ASSESSMENT DATA GENERATING PROCESSOR 552

CONTROLLER 510

UI 520

OPHTHALMIC APPARATUS

CROSS-REFERENCE TO RELATED APPLICATIONS

This application is a national stage (under 35 U.S.C. 371) of International Patent Application No. PCT/JP2020/047608, filed Dec. 21, 2020, claiming priority to Japanese Patent Application No. 2020-013120, filed Jan. 30, 2020, both of which are herein incorporated by reference in their entirety.

TECHNICAL FIELD

The present disclosure relates generally to an ophthalmic apparatus, a method of controlling the same, and a recording medium.

BACKGROUND OF THE INVENTION

Anterior eye segment analysis techniques using optical coherence tomography (OCT) are known. One of these techniques is corner angle analysis conducted for glaucoma diagnosis, especially diagnosis of angle closure glaucoma (see, for example, PATENT DOCUMENTS 1 to 4).

Corner angle analysis uses calculation of a parameter, which is related to a corner angle (angle of anterior chamber) located between a cornea and an iris, based on an OCT image of an anterior segment. In corner angle parameter calculation, it is necessary to detect both the cornea and the iris in the OCT image to determine the position of the corner angle. For accurate and precise corner angle position detection, both the cornea and the iris should be depicted with high degree of image quality.

PATENT DOCUMENT 1: Japanese Unexamined Patent Application Publication No. 2011-147611

PATENT DOCUMENT 2: Japanese Unexamined Patent Application Publication No. 2013-226383

PATENT DOCUMENT 3: Japanese Unexamined Patent Application Publication (Translation of PCT Application) No. 2014-500096

PATENT DOCUMENT 4: Japanese Unexamined Patent Application Publication No. 2015-43814

BRIEF SUMMARY OF THE INVENTION

However, existing or conventional techniques of OCT anterior segment analysis cannot determine whether both the cornea and the iris are depicted with a sufficient degree of image quality, making it difficult to accurately determine the position of a corner angle. This has resulted in various problems, such as deterioration of the quality (e.g., accuracy, precision, etc.) of corner angle analysis, re-execution of OCT scanning, and lengthening of examination time.

In addition to corner angle analysis, similar problems have occurred in various kinds of OCT anterior segment analysis that requires the detection of two or more parts (sites, tissues, locations, positions, etc.) of an eye. For example, in anterior chamber depth analysis, which determines the distance between the cornea and the crystalline lens, both the cornea and the crystalline lens should be depicted with high degree of image quality.

A purpose of the present disclosure is to make an improvement in OCT anterior segment analysis.

An ophthalmic apparatus of some aspect examples may include: an image acquiring unit configured to acquire an anterior segment image constructed based on data collected from an anterior segment of a subject's eye by optical coherence tomography (OCT) scanning; a part image identifying processor configured to perform identification of two or more part images respectively corresponding to two or more parts of the anterior segment from the anterior segment image acquired by the image acquiring unit; a part image assessing processor configured to perform image quality assessment of each of the two or more part images identified by the part image identifying processor; and an anterior segment image assessing processor configured to perform image quality assessment of the anterior segment image based on two or more pieces of assessment data respectively obtained for the two or more part images by the part image assessing processor.

In an ophthalmic apparatus of some aspect examples, the part image assessing processor may include: an assessment region setting processor configured to perform setting of an assessment region for each of the two or more part images identified by the part image identifying processor; and an assessment data generating processor configured to perform generation of assessment data by analyzing the assessment region set by the assessment region setting processor.

In an ophthalmic apparatus of some aspect examples, the assessment region setting processor may further be configured to perform the setting of the assessment region for each of the two or more part images identified by the part image identifying processor in such a manner that the assessment region includes a first region and a second region. The first region is at least part of a corresponding part image, and the second region is located outside the corresponding part image.

In an ophthalmic apparatus of some aspect examples, the assessment region setting processor may further be configured to perform the setting of the assessment region in such a manner that the first region and the second region are adjacent to each other.

In an ophthalmic apparatus of some aspect examples, the part image identifying processor may further be configured to perform identification of a first part image group if the anterior segment image acquired by the image acquiring unit is a wide angle image, and to perform identification of a second part image group that is different from the first part image group if the anterior segment image is a non-wide angle image.

In an ophthalmic apparatus of some aspect examples, a number of part images included in the first part image group and a number of part images included in the second part image group may be different from each other.

In an ophthalmic apparatus of some aspect examples, the part image identifying processor may further be configured to perform the identification of the part image by applying edge detection to the anterior segment image acquired by the image acquiring unit.

In an ophthalmic apparatus of some aspect examples, the part image identifying processor may further be configured to perform identification of a cornea image and identification of an iris image from the anterior segment image acquired by the image acquiring unit, the part image assessing processor may further be configured to perform image quality assessment of the cornea image and image quality assessment of the iris image, and the anterior segment image assessing processor may further be configured to perform the image quality assessment of the anterior segment image based on assessment data obtained for the cornea image and assessment data obtained for the iris image.

In an ophthalmic apparatus of some aspect examples, the part image assessing processor may include: an assessment region setting processor configured to perform setting of a cornea assessment region for the cornea image, and to perform setting of an iris assessment region for the iris image; and an assessment data generating processor configured to perform generation of cornea assessment data by analyzing the cornea assessment region, and to perform generation of iris assessment data by analyzing the iris assessment region.

In an ophthalmic apparatus of some aspect examples, the assessment region setting processor may further be configured to perform the setting of the cornea assessment region in such a manner that the cornea assessment region includes an intra-cornea region and an extra-cornea region, wherein the intra-cornea region is at least part of the cornea image and the extra-cornea region is located outside the cornea image, and the assessment region setting processor may further be configured to perform the setting of the iris assessment region in such a manner that the iris assessment region includes an intra-iris region and an extra-iris region, wherein the intra-iris region is at least part of the iris image and the extra-iris region is located outside the iris image.

In an ophthalmic apparatus of some aspect examples, the assessment region setting processor may further be configured to perform the setting of the cornea assessment region in such a manner that the intra-cornea region and the extra-cornea region are adjacent to each other, and the assessment region setting processor may further be configured to perform the setting of the iris assessment region in such a manner that the intra-iris region and the extra-iris region are adjacent to each other.

In an ophthalmic apparatus of some aspect examples, the part image identifying processor may further be configured to perform the identification of the cornea image by identifying a first cornea image and a second cornea image, wherein the first cornea image is located in a vicinity of a first frame edge of the anterior segment image and the second cornea image is located in a vicinity of a second frame edge opposite to the first frame edge, and to perform the identification of the iris image by identifying a first iris image and a second iris image, wherein the first iris image is located in a vicinity of the first frame edge and the second iris image is located in a vicinity of the second frame edge, if the anterior segment image acquired by the image acquiring unit is a wide angle image, and the part image identifying processor may further be configured to perform the identification of the cornea image by identifying a single cornea image, and to perform the identification of the iris image by identifying a single iris image, if the anterior segment image is a non-wide angle image.

In an ophthalmic apparatus of some aspect examples, the part image identifying processor may further be configured to perform the identification of the cornea image by applying edge detection to the anterior segment image acquired by the image acquiring unit, and to perform the identification of the iris image by applying edge detection to the anterior segment image acquired by the image acquiring unit.

In an ophthalmic apparatus of some aspect examples, the part image identifying processor may further be configured to perform identification of one or both of an anterior corneal surface image and a posterior corneal surface image and identification of an anterior iridic surface image by the edge detection, the part image identifying processor may further be configured to perform the identification of the cornea image based on the one or both of the anterior corneal surface image and the posterior corneal surface image, and the part image identifying processor may further be configured to perform the identification of the iris image based on the anterior iridic surface image.

In an ophthalmic apparatus of some aspect examples, the part image identifying processor may further be configured to perform the identification of the anterior corneal surface image by identifying an edge where a gradient direction is toward a frame edge of the anterior segment image and where a gradient value is equal to or greater than a predetermined threshold value.

In an ophthalmic apparatus of some aspect examples, the part image identifying processor may further be configured to perform the identification of the posterior corneal surface image by identifying an edge where a gradient direction is toward a central region of a frame of the anterior segment image and where a gradient value is equal to or greater than a predetermined threshold value.

An ophthalmic apparatus of some aspect examples may further include an image correcting processor configured to perform correction of a pixel aspect ratio of the anterior segment image.

In an ophthalmic apparatus of some aspect examples, the image correcting processor may further be configured to perform correction of the pixel aspect ratio of the anterior segment image with an image quality assessed to be satisfactory by the anterior segment image assessing processor.

An ophthalmic apparatus of some aspect examples may further include a corner angle analyzing processor configured to perform calculation of a predetermined corner angle parameter by analyzing the anterior segment image whose pixel aspect ratio has been corrected by the image correcting processor.

In an ophthalmic apparatus of some aspect examples, the anterior segment image assessing processor may further be configured to perform the image quality assessment of the anterior segment image by applying a predetermined statistical calculation to the two or more pieces of assessment data obtained by the part image assessing processor.

In an ophthalmic apparatus of some aspect examples, the anterior segment image assessing processor may further be configured to perform the image quality assessment of the anterior segment image by applying at least an averaging calculation to the two or more pieces of assessment data.

In an ophthalmic apparatus of some aspect examples, the anterior segment image assessing processor may further be configured to perform the image quality assessment of the anterior segment image by performing at least selection of assessment data corresponding to a lowest image quality by comparing the two or more pieces of assessment data.

An ophthalmic apparatus of some aspect examples may further include an analyzing processor configured to perform calculation of a predetermined anterior segment parameter by analyzing the anterior segment image.

In an ophthalmic apparatus of some aspect examples, the image acquiring unit may include: a data collector configured to collect data by applying OCT scanning to the anterior segment; and an image constructing processor configured to construct the anterior segment image based on the data collected by the data collector.

In an ophthalmic apparatus of some aspect examples, if an image quality of the anterior segment image is assessed to be unsatisfactory by the anterior segment image assessing processor, the data collector may collect another data by applying OCT scanning to the anterior segment again, and the image constructing processor may construct another anterior segment image based on the another data collected by the data collector.

In an ophthalmic apparatus of some aspect examples, the image acquiring unit may include a receiver that receives the anterior segment image from outside.

An ophthalmic apparatus of some aspect examples may further include a signal output unit configured to output a signal representing a need for re-application of OCT scanning to the subject's eye if an image quality of the anterior segment image is assessed to be unsatisfactory by the anterior segment image assessing processor.

Some aspect examples is a method of controlling an ophthalmic apparatus that includes a processor, the method including: causing the processor to perform identification of two or more part images respectively corresponding to two or more parts of an anterior segment of a subject's eye from an anterior segment image constructed based on data collected from the anterior segment by optical coherence tomography (OCT) scanning; causing the processor to perform image quality assessment of each of the two or more part images; and causing the processor to perform image quality assessment of the anterior segment image based on two or more pieces of assessment data respectively obtained for the two or more part images.

Some aspect examples is a computer-readable non-transitory recording medium storing a program that causes a computer to execute the method of an aspect example.

Effect of the Invention

An aspect example is capable of making an improvement in OCT anterior segment analysis.

BRIEF DESCRIPTION OF THE SEVERAL VIEWS OF THE DRAWING

FIG. 3 is a diagram of an example of a configuration of an ophthalmic apparatus according to an aspect example.
FIG. 5B is a diagram illustrating an example of processing executed by an ophthalmic apparatus according to an aspect example.
FIG. 7B is a diagram illustrating an example of processing executed by an ophthalmic apparatus according to an aspect example.

FIG. 10 is a flowchart illustrating an example of an operation executed by an ophthalmic apparatus according to an aspect example.
FIG. 12 is a diagram of an example of a configuration of an ophthalmic apparatus according to an aspect example.

DETAILED DESCRIPTION OF THE INVENTION

Figure 1:
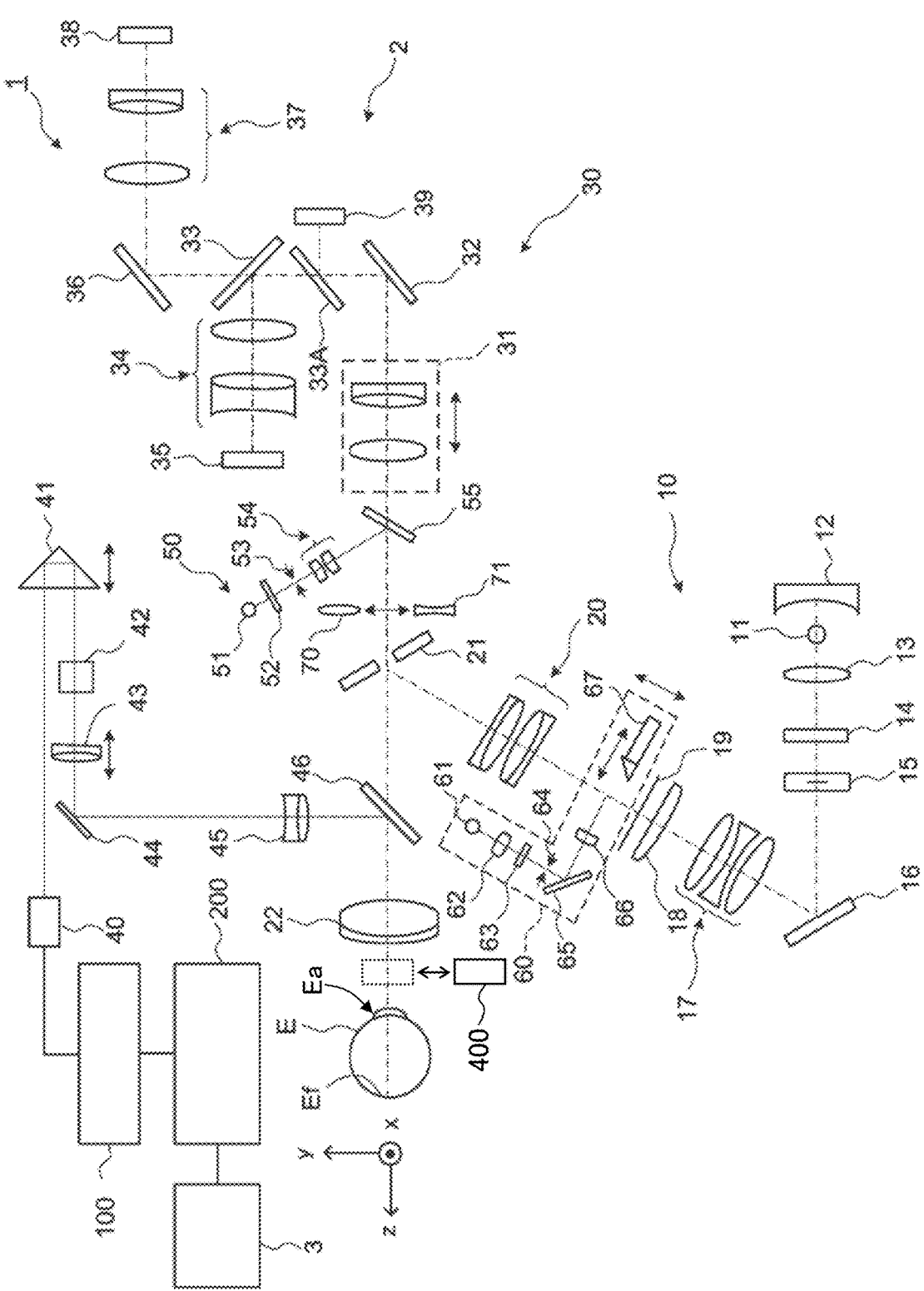
FIG. 1 is a diagram of an example of a configuration of an ophthalmic apparatus according to an aspect example.

The present disclosure describes several aspect examples of embodiments of an ophthalmic apparatus, a method of controlling the same, a program, and a recording medium with referring to the drawings. Any matters and items disclosed by the documents cited in the present disclosure and any other known technologies and techniques may be incorporated with the aspect examples described in the present disclosure. Note that "image data" and an "image" formed based on this image data are not distinguished in the present disclosure unless otherwise mentioned. Similarly, a "site (part, tissue, etc.)" of a subject's eye and an "image" of this site are not distinguished in the present disclosure unless otherwise mentioned.

An ophthalmic apparatus according to some aspect examples is configured to be capable of measuring and imaging the anterior segment of a living eye by applying Fourier domain OCT techniques (e.g., swept source OCT techniques). The types of OCT techniques applicable to aspect examples are not limited to swept source OCT techniques, and spectral domain OCT techniques or time domain OCT techniques may be applied to some aspect examples.

An ophthalmic apparatus according to some aspect examples may be configured to be capable of executing processing of an image acquired by a modality other than OCT. For example, some aspect examples may be configured to be capable of executing processing of an image acquired by any of a fundus camera (retinal camera), a laser scanning ophthalmoscope (SLO), a slit lamp microscope, and an ophthalmic surgical microscope. An ophthalmic apparatus according to some aspect examples may include one or more of a fundus camera, an SLO, a slit lamp microscope, and an ophthalmic surgical microscope.

An ophthalmic apparatus according to some aspect examples is configured to acquire an image constructed based on data collected from the anterior segment of a living eye by applying OCT scanning, and to apply processing to this image. This image is referred to as an anterior segment image.

In some aspect examples, the method and technique of acquiring an anterior segment image is freely selected or designed. For example, an ophthalmic apparatus according to some aspect examples may include a configuration of collecting data by applying OCT scanning to the anterior segment of a living eye and a configuration of constructing an anterior segment image based on the data collected.

An ophthalmic apparatus according to some aspect examples may have a function of receiving an anterior segment image of a living eye from outside. In some examples, an anterior segment image of a living eye is acquired by using an OCT apparatus and this anterior segment image is stored in a medical image management system such as a picture archiving and communication system (PACS). An ophthalmic apparatus according to some aspect examples is configured to access to the medical image management system and obtain an anterior segment image.

In addition to descriptions of such an ophthalmic apparatus, the present disclosure gives descriptions of a method of controlling an ophthalmic apparatus, descriptions of a program of causing a computer to execute such a method, and descriptions of a recording medium storing such a program.

At least one or more of the functions of the elements described in the present disclosure are implemented by using a circuit configuration (circuitry) or a processing circuit configuration (processing circuitry). The circuitry or the processing circuitry includes any of the followings, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), an existing or conventional circuit configuration or circuitry, and any combination of these. A processor is considered to be processing circuitry or circuitry that includes a transistor and/or another circuitry. In the present disclosure, circuitry, a unit, a means, or a term similar to these is hardware that executes at least one or more functions disclosed herein, or hardware that is programmed to execute at least one or more functions disclosed herein. Hardware may be the hardware disclosed herein, or alternatively, known hardware that is programmed and/or configured to execute at least one or more functions described herein. In the case in which the hardware is a processor, which may be considered as a certain type of circuitry, then circuitry, a unit, a means, or a term similar to these is a combination of hardware and software. In this case, the software is used to configure the hardware and/or the processor.

<Configuration of Ophthalmic Apparatus>

The ophthalmic apparatus 1 of an aspect example shown in FIG. 1 is a multifunction apparatus that is a combination of an OCT apparatus and a fundus camera, and has both the function of applying OCT scanning to an anterior eye segment and the function of conducting photography of an anterior eye segment. The ophthalmic apparatus 1 includes the fundus camera unit 2, the OCT unit 100, and the arithmetic and control unit 200. The fundus camera unit 2 is provided with an element group (e.g., optical elements, mechanisms, etc.) for acquiring a front image of a subject's eye. The OCT unit 100 includes part of an element group (e.g., optical elements, mechanisms, etc.) for conducting OCT scanning. Another part of the element group for conducting OCT scanning is provided in the fundus camera unit 2. The arithmetic and control unit 200 includes one or more processors configured and programmed to execute various processes (e.g., calculations, controls, etc.), and one or more storage devices (memories). In addition to these elements, the ophthalmic apparatus 1 may also include any elements and/or any units such as a member for supporting the face of the subject, an attachment for switching or changing sites of a subject's eye to which OCT scanning is applied. Here, examples of the member for supporting the face of the subject include a chin rest and a forehead rest.

A description is now given of some examples of the attachment for switching or changing sites of a subject's eye to which OCT scanning is applied. An example attachment includes a lens group (lens unit). The anterior segment OCT attachment 400 (the attachment for anterior segment OCT 400) includes a lens group used for switching sites of the subject's eye E to which OCT scanning is applied between the posterior segment and the anterior segment. The anterior segment OCT attachment 400 may have the same configuration as the optical unit disclosed in Japanese Unexamined Patent Application Publication No. 2015-160103.

As illustrated in FIG. 1, the anterior segment OCT attachment 400 is inserted between the objective lens 22 and the subject's eye E. In the state in which the anterior segment OCT attachment 400 is placed in the optical path, the ophthalmic apparatus 1 can apply OCT scanning to the anterior segment of the subject's eye E. On the other hand, in the state in which the anterior segment OCT attachment 400 is removed from the optical path, the ophthalmic apparatus 1 can apply OCT scanning to the posterior segment of the subject's eye E. The movement (insertion and removal) of the anterior segment OCT attachment 400 is performed by hand or by machine (manually or automatically).

An ophthalmic apparatus of some aspect examples may be configured to apply OCT scanning to a posterior segment in the state in which an attachment is inserted in an optical path and to apply OCT scanning to an anterior segment in the state in which this attachment is removed from this optical path. Sites of a subject's eye to which OCT scanning is applied switched by an attachment are not limited to the combination of anterior segment and posterior segment, and may be any combinations of ocular sites. Also, a configuration for switching sites of a subject's eye to which OCT scanning is applied is not limited to attachments like the one described above (lens group, lens unit, optical unit), and some examples of this configuration may include one or more lenses movable along an optical path.

<Fundus Camera Unit 2>

The fundus camera unit 2 includes elements (e.g., optical elements, mechanisms, etc.) for acquiring digital images (digital photographs, digital pictures) by conducting photography of the subject's eye E (e.g., the anterior segment Ea, fundus Ef, etc.). The digital images of the subject's eye E acquired are front images (en face images) such as observation images and photographed images. An observation image is obtained, for example, by capturing a moving image using near-infrared light, and may be used for alignment, focusing, tracking, and other operations. A photographed image is a still image obtained using visible flash light or infrared flash light, for example. A photographed image may be used for diagnosis, analysis, or other purposes.

The fundus camera unit 2 includes the illumination optical system 10 and the photographing optical system 30. The illumination optical system 10 projects illumination light onto the subject's eye E. The photographing optical system 30 detects return light of the illumination light from the subject's eye E. Measurement light entered from the OCT unit 100 is directed to the subject's eye E through an optical path in the fundus camera unit 2, and return light of this measurement light from the subject's eye E is directed to the OCT unit 100 through the same optical path.

Light emitted by the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the area surrounding the aperture part) of the aperture mirror 21, penetrates the dichroic mirror 46, and refracted by the objective lens 22, thereby illuminating the subject's eye E. Return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Furthermore, the return light of the observation illumination light passes through the half mirror 33A, is reflected by the dichroic mirror 33, and forms an image on the light receiving surface of the image sensor 35 by the imaging lens 34. The image sensor 35 detects the return light at a predetermined frame rate. The photographing optical system 30 is adjusted to be focused on the fundus Ef or the anterior segment Ea.

Light emitted by the photographing light source 15 (referred to as photographing illumination light) passes through the same route as the route of the observation illumination light and is projected onto the subject's eye E. Return light of the photographing illumination light from the subject's eye E passes through the same route as the route of the return light of the observation illumination light to the dichroic mirror 33, passes through the dichroic mirror 33, is reflected by the mirror 36, and forms an image on the light receiving surface of the image sensor 38 by the imaging lens 37.

The liquid crystal display (LCD) 39 displays a fixation target (fixation target image). Part of a light beam output from the LCD 39 is reflected by the half mirror 33A and the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

Varying the display position of the fixation target image on the LCD 39 can be used to change fixation position (also referred to as fixation direction) of the subject's eye E by the fixation target. That is, the line of sight of the subject's eye E can be guided in a desired direction by changing the fixation position. The ophthalmic apparatus 1 may be provided with a graphical user interface (GUI) used for designation of a desired fixation position.

Configurations for presenting, to the subject's eye E, a fixation target in such a manner that a fixation position can be changed, are not limited to a display device such as LCD. For example, a fixation matrix may be used, in place of such a display device, that includes a plurality of light emitting elements (e.g., light emitting diodes or the like) arranged in a matrix pattern (array pattern). In this example case, a fixation position can be changed by selecting and turning on a light emitting element. In another example case, a fixation position can be changed by means of one or more movable light emitting elements.

The alignment optical system 50 generates an alignment indicator used for alignment of the optical system with respect to the subject's eye E. Alignment light emitted by the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. Return light of the alignment light from the subject's eye E passes through the same route as the route of the return light of the observation illumination light and is guided to the image sensor 35. An image detected by the image sensor 35 (alignment indicator image) is used for performing manual alignment and/or automatic alignment.

As in existing or conventional techniques, the alignment indicator image of the present example includes two bright spot images whose positions change depending on alignment states (alignment conditions). When the relative position between the subject's eye E and the optical system changes in the xy direction, the two bright spot images are shifted together in the xy direction. When the relative position between the subject's eye E and the optical system changes in the z direction, the relative position (the distance) between the two bright spot images changes. In the state in which the distance between the subject's eye E and the optical system in the z direction matches with a working distance set in advance, the two bright spot images overlap each other. In the state in which the position of the subject's eye E matches with the position of the optical system in the xy direction, the two bright spot images are located within or near an alignment target set in advance. In the state in which not only the distance between the subject's eye E and the optical system in the z direction matches with the working distance but also the position of the subject's eye E matches with the position of the optical system in the xy direction, the two bright spot images overlap each other and are located within the alignment target.

When conducting automatic alignment, the data processor 230 detects the positions of the two bright spot images, and the main controller 211 controls the movement mechanism 150 (described later) on the basis of the positional relationship between the two bright spot images and the alignment target. When conducting manual alignment, the main controller 211 displays the two bright spot images together with an observation image of the subject's eye E on the display 241, and the user manipulates the operation device 242 to operate the movement mechanism 150 while monitoring the two bright spot images displayed.

The methods and techniques of alignment are not limited to those described above. An ophthalmic apparatus according to some aspect examples may include an alignment unit configured to perform the following processes (see, for example, Japanese Unexamined Patent Application Publication No. 2013-248376): a process of acquiring two or more photographed images of an anterior segment of a subject's eye by substantially simultaneously conducting two or more operations of anterior segment photography of the anterior segment from two or more different directions; a process of calculating a three dimensional position of the subject's eye by analyzing the two or more photographed images; and a process of moving an optical system based on the three dimensional position calculated.

The focusing optical system 60 generates a split indicator used for focus adjustment (focusing, focusing operation) with respect to the subject's eye E. The focusing optical system 60 is moved along the optical path of the illumination optical system 10 in conjunction with movement of the photography focusing lens 31 along the optical path of the photographing optical system 30. The optical path of the illumination optical system 10 is referred to as the illumination optical path, and the optical path of the photographing optical system 30 is referred to as the photographing optical path. The reflection rod 67 is inserted into and removed from the illumination optical path. The reflective surface of the reflection rod 67 is inserted into the illumination optical path and placed in an oblique orientation before performing focus adjustment. Focus light emitted by the LED 61 passes through the relay lens 62, is split into two light beams by the split indicator plate 63, and passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. Return light of the focus light from the subject's eye E passes through the same route as the route of the return light of the alignment light and is guided to the image sensor 35. An image detected by the image sensor 35 (split indicator image) is used for performing manual focusing and/or automatic focusing.

The diopter correction lenses 70 and 71 are selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for digital photography and the optical path for OCT scanning. The optical path for digital photography includes the illumination optical path and the photographing optical path. The optical path for OCT scanning is referred to as a sample arm. The dichroic mirror 46 reflects light of wavelength bands used for OCT scanning while transmitting light for digital photography. Listed from the OCT unit 100 side, the sample arm includes the collimator lens unit 40, the retroreflector 41, the dispersion compensation member 42, the OCT focusing lens 43, the optical scanner 44, and the relay lens 45.

The retroreflector 41 is movable in the directions indicated by the arrow in FIG. 1. These directions are the direction in which the measurement light LS is incident onto the subject's eye E and the direction in which return light of the measurement light LS from the subject's eye E travels. With this movement of the retroreflector 41, the length of the sample arm is changed. This change in the sample arm length may be used for operations such as optical path length correction on the basis of eye axial length, optical path length correction on the basis of corneal shape and/or eye fundus shape, and adjustment or regulation of interference conditions or states.

The dispersion compensation member 42, together with the dispersion compensation member 113 (described later) arranged in the reference arm, acts to equalize the dispersion characteristics of the measurement light LS and the dispersion characteristics of the reference light LR with each other.

The OCT focusing lens 43 is movable in the directions indicated by the arrow in FIG. 1 (that is, movable along the optical axis of the sample arm) in order to perform focus adjustment of the sample arm. With this movement of the OCT focusing lens 43, the focus conditions or the focus states (focal position, focal length) of the sample arm is changed. The ophthalmic apparatus 1 may be configured to be capable of executing interlocking control between the movement of the photography focusing lens 31, the movement of the focusing optical system 60, and the movement of the OCT focusing lens 43.

The optical scanner 44 is placed substantially at a position optically conjugate with the pupil of the subject's eye E. The optical scanner 44 deflects the measurement light LS guided by the sample arm. The optical scanner 44 of some examples may be a deflection system capable of two dimensional scanning that includes a deflector for performing scanning in the x direction and a deflector for performing scanning in the y direction (x-scanner and y-scanner). The optical scanner 44 of some examples may be a galvanometer scanner including two galvanometer mirrors. In some typical examples, one of the two deflectors is arranged at a position optically conjugate with the pupil of the subject's eye E, or the position optically conjugate with the pupil is arranged at a position between the two deflectors. Such arrangement makes it capable of OCT scanning of the fundus Ef in which the measurement light LS is deflected around a pivot located at a position in (or near) the pupil of the subject's eye E, which makes it possible to apply OCT scanning to a wide (broad) area of the fundus Ef.

In the present aspect, the optical scanner 44 is placed at a position substantially optically conjugate with the pupil of the subject's eye E as described above when the anterior segment OCT attachment 400 is not placed in the optical path. On the other hand, the optical scanner 44 is placed at a position substantially optically conjugate with a position between the anterior segment Ea and the anterior segment OCT attachment 400 when the anterior segment OCT attachment 400 is placed in the optical path. More specifically, in the case in which the anterior segment OCT attachment 400 is removed from the optical path, for example, one of the x-scanner and the y-scanner is placed at a position substantially optically conjugate with the pupil, or a position between the x-scanner and the y-scanner is placed at a position substantially optically conjugate with the pupil. Further, in the case in which the anterior segment OCT attachment 400 is inserted in the optical path, for example, one of the x-scanner and the y-scanner is placed at a position substantially optically conjugate with a position between the anterior segment Ea and the anterior segment OCT attachment 400, or a position between the x-scanner and the y-scanner is placed at a position substantially optically conjugate with a position between the anterior segment Ea and the anterior segment OCT attachment 400.

<OCT Unit 100>

Figure 2:
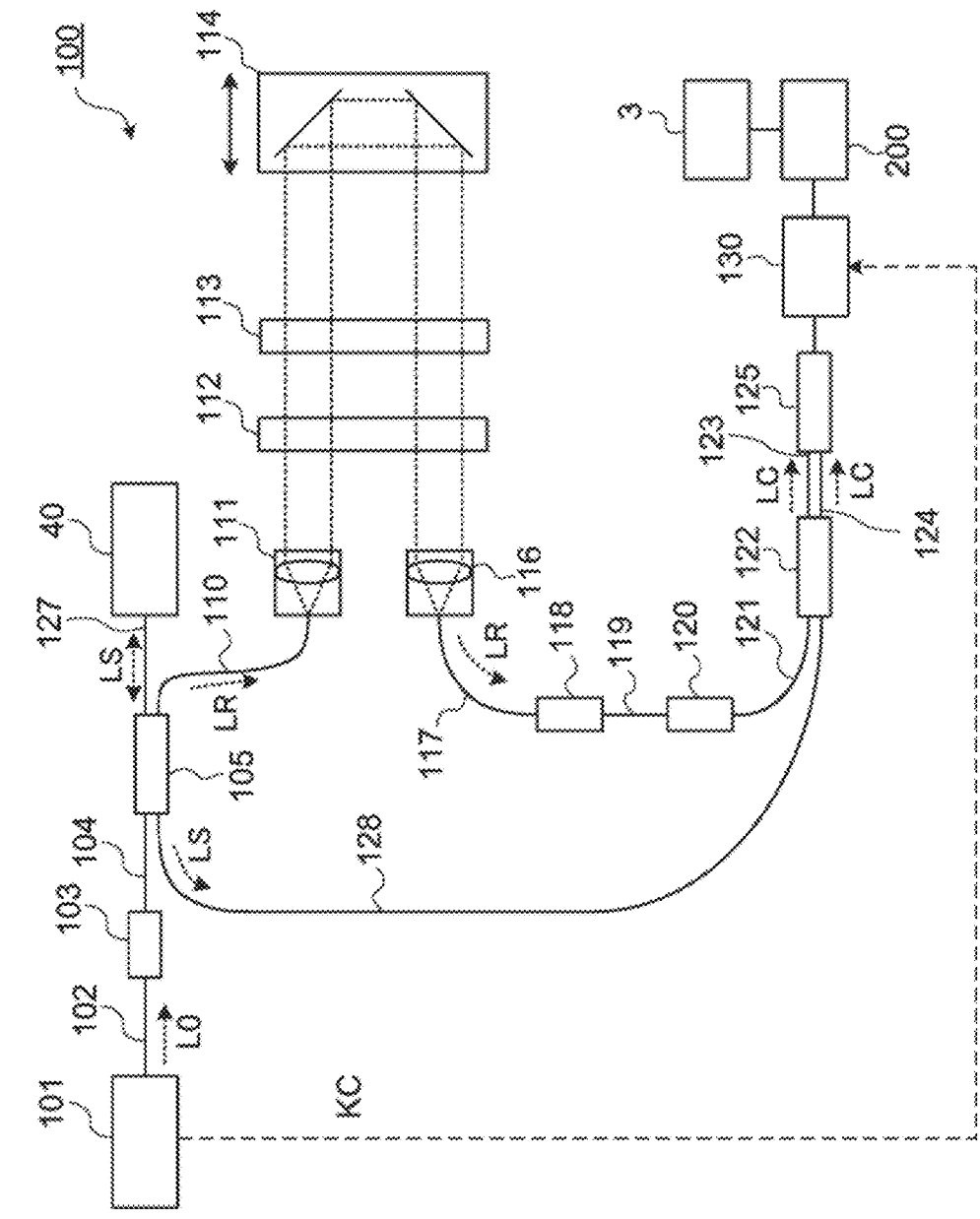
FIG. 2 is a diagram of an example of a configuration of an ophthalmic apparatus according to an aspect example.

As illustrated in FIG. 2, the OCT unit 100 is provided with an optical system and mechanisms for performing swept source OCT. This optical system includes an interference optical system. This interference optical system is configured to split light emitted by a wavelength tunable light source (wavelength sweeping light source) into measurement light and reference light, to generate interference light by superposing return light of the measurement light from the subject's eye E on the reference light that has been guided by a reference optical path (reference arm), and to detect this interference light. A result of this interference light detection (detection signal) obtained by the interference optical system, is a signal representing a spectrum of the interference light. This detection signal (interference signal) is sent to the arithmetic and control unit 200 (the image data constructing unit 220).

The light source unit 101 of some examples includes a near-infrared wavelength tunable laser configured to vary the wavelengths of emitted light at high speed. The light LO output from the light source unit 101 is guided to the polarization controller 103 through the optical fiber 102. The polarization controller 103 is configured to perform regulation (adjustment) of the polarization condition (polarization state) of the light LO. Further, the light LO is guided to the fiber coupler 105 through the optical fiber 104. The fiber coupler 105 is configured to split the light LO into the measurement light LS and the reference light LR. The optical path of the measurement light LS is referred to as the sample arm or the like, and the optical path of the reference light LR is referred to as the reference arm or the like.

The reference light LR is guided through the optical fiber 110 to the collimator 111, is converted into a parallel light beam by the collimator 111, travels through the optical path length correction member 112 and the dispersion compensation member 113, and is guided to the retroreflector 114. The optical path length correction member 112 is an optical element for equalizing the optical path length of the reference light LR and the optical path length of the measurement light LS with each other. The dispersion compensation member 113 is an optical element for equalizing the dispersion characteristics of the reference light LR and the dispersion characteristics of the measurement light LS with each other, together with the dispersion compensation member 42 disposed in the sample arm. The retroreflector 114 is movable along the optical path of the reference light LR that is incident onto the retroreflector 114. With this, the length of the reference arm is changed. This change in the reference arm length may be used for operations such as optical path length correction on the basis of eye axial length, optical path length correction on the basis of corneal shape and/or eye fundus shape, and adjustment or regulation of interference conditions or states.

The reference light LR that has passed through the retroreflector 114 travels through the dispersion compensation member 113 and the optical path length correction member 112, is converted from a parallel light beam to a convergent light beam by the collimator 116, and is incident onto the optical fiber 117. The reference light LR that has entered the optical fiber 117 is guided to the polarization controller 118, and the polarization state of the reference light LR is regulated by the polarization controller 118. The polarization controller 118 is an optical device for interference condition regulation (interference condition adjustment, interference state regulation, interference state adjustment). The polarization controller 118 is used for optimizing the strength of interference (coherence) between the measurement light LS and the reference light LR, for example. The reference light LR output from the polarization controller 118 is guided to the attenuator 120 through the optical fiber 119, and the amount of light of the reference light LR is regulated by the attenuator 120. Subsequently, the reference light LR is guided to the fiber coupler 122 through the optical fiber 121.

Meanwhile, the measurement light LS generated by the fiber coupler 105 is guided through the optical fiber 127 to the collimator lens unit 40 and is converted to a parallel light beam by the collimator lens unit 40. The measurement light LS output from the collimator lens unit 40 passes through the retroreflector 41, the dispersion compensation member 42, the OCT focusing lens 43, the optical scanner 44, and the relay lens 45, is reflected by the dichroic mirror 46, and is refracted by the objective lens 22, thereby being projected onto the subject's eye E. Note that when the anterior segment OCT attachment 400 is placed in the sample arm, the measurement light LS reflected by the dichroic mirror 46 is projected onto the subject's eye E (the anterior segment Ea) via the objective lens 22 and the anterior segment OCT attachment 400. The measurement light LS is reflected and scattered at various depth positions of the subject's eye E. Return light of the measurement light LS from the subject's eye E travels along the same route as the outward way in the opposite direction to the fiber coupler 105, and then reaches the fiber coupler 122 through the optical fiber 128.

The fiber coupler 122 superposes the measurement light LS reached here through the optical fiber 128 with the reference light LR reached here through the optical fiber 121 to generate interference light. The fiber coupler 122 splits the interference light generated by the fiber coupler 122 at a predetermined splitting ratio (e.g., 1 to 1) to generate a pair of interference light LC. The pair of interference light LC is guided to the detector 125 through the optical fibers 123 and 124, respectively.

The detector 125 of some examples includes a balanced photo diode. This balanced photodiode includes a pair of photodetectors that detects the pair of the interference light LC respectively. The balanced photodiode outputs a difference signal between a pair of detection signals corresponding to the pair of the interference light LC respectively obtained by the pair of photodetectors. The detector 125 sends this output (difference signal, detection signal) to the data acquisition system (DAQ) 130.

The clock KC is supplied from the light source unit 101 to the data acquisition system 130. The clock KC is generated in the light source unit 101 in synchronization with the output timings of individual wavelengths varied over a predetermined wavelength range by the wavelength tunable light source. The light source unit 101 of some examples is configured to split the light LO of the individual output wavelengths to generate two pieces of split light, to apply an optical delay to one of the two pieces of split light, to superpose the resulting two pieces of split light with one another, to detect the resulting superposed light, and to generate the clock KC based on the detection result of the superposed light. Based on the clock KC, the data acquisition system 130 performs sampling of the detection signal input from the detector 125. The data acquisition system 130 sends the result of this sampling to the arithmetic and control unit 200.

The present aspect example is provided with both an element for changing the sample arm length (e.g., the retroreflector 41) and an element for changing the reference arm length (e.g., the retroreflector 114 or a reference mirror). However, some other aspect examples may be provided with only either one of these two elements. An element for changing the difference between the sample arm length and the reference arm length (i.e., an element for changing the optical path length difference) is not limited to these examples described herein, and may be freely selected element such as any optical member and/or any mechanism.

As described above, swept source OCT is a technique including the following processes: a process of splitting light emitted by a wavelength tunable light source into measurement light and reference light; a process of generating interference light by superposing return light of the measurement light from a sample and the reference light; a process of detecting the interference light by a photodetector; and a process of constructing an image of the sample by applying signal processing including a Fourier transform to detection data collected corresponding to wavelength sweeping (change in emitted wavelengths) and scanning with the measurement light.

Spectral domain OCT, an alternative to swept source OCT, is a technique including the following processes: a process of splitting light emitted by a low coherence light source (broad band light source, wide band light source) into measurement light and reference light; a process of generating interference light by superposing return light of the measurement light from a sample and the reference light; a process of detecting a spectral distribution (spectral components) of the interference light by a spectrometer; and a process of constructing an image of the sample by applying signal processing including a Fourier transform to the spectral distribution detected.

In short, swept source OCT can be said to be an OCT technique of acquiring a spectral distribution of interference light in a time-divisional manner while spectral domain OCT can be said to be an OCT technique of acquiring a spectral distribution of interference light in a space-divisional manner.

<Control System and Processing System>

Figure 3:
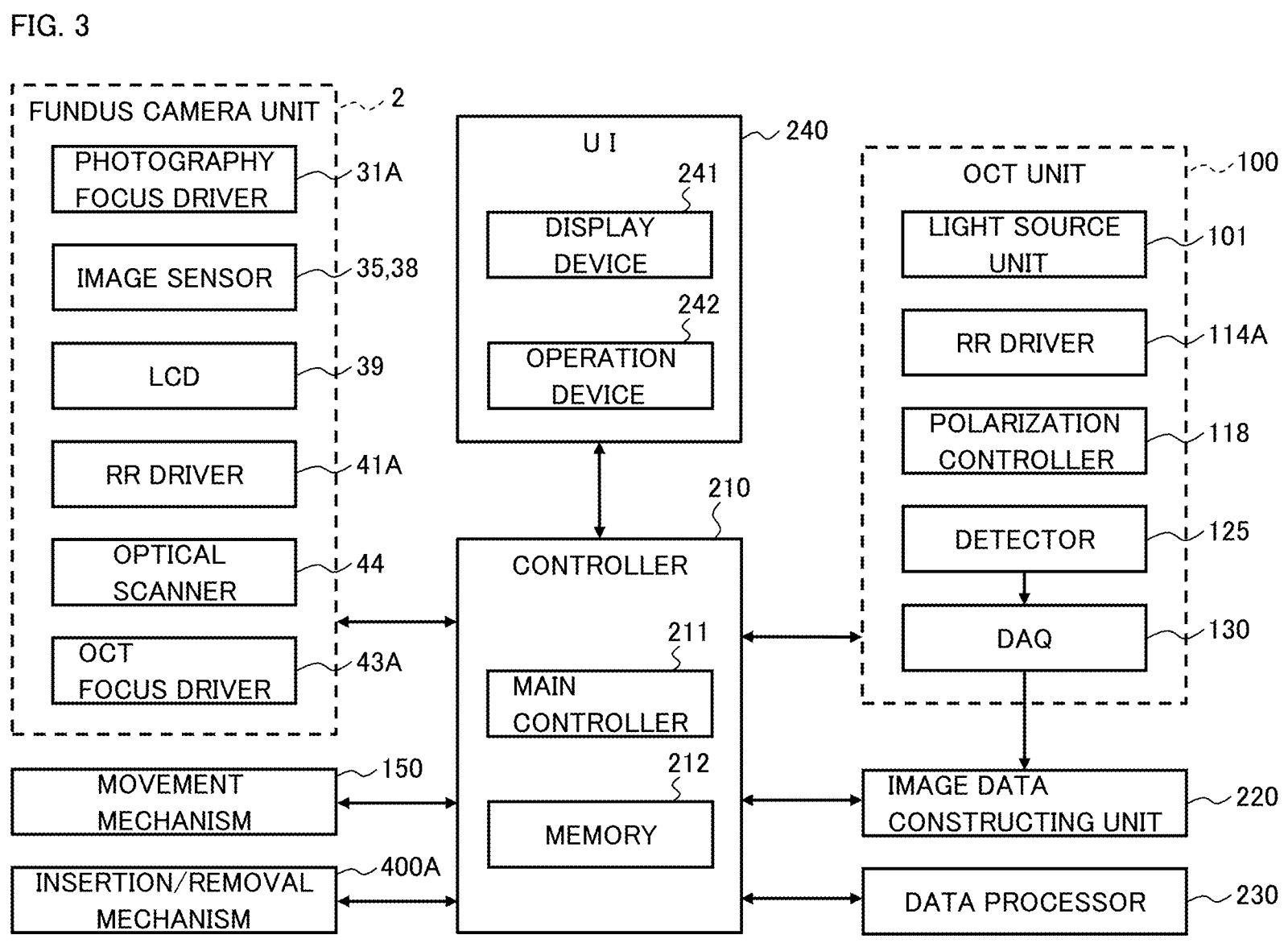
Figure 4:
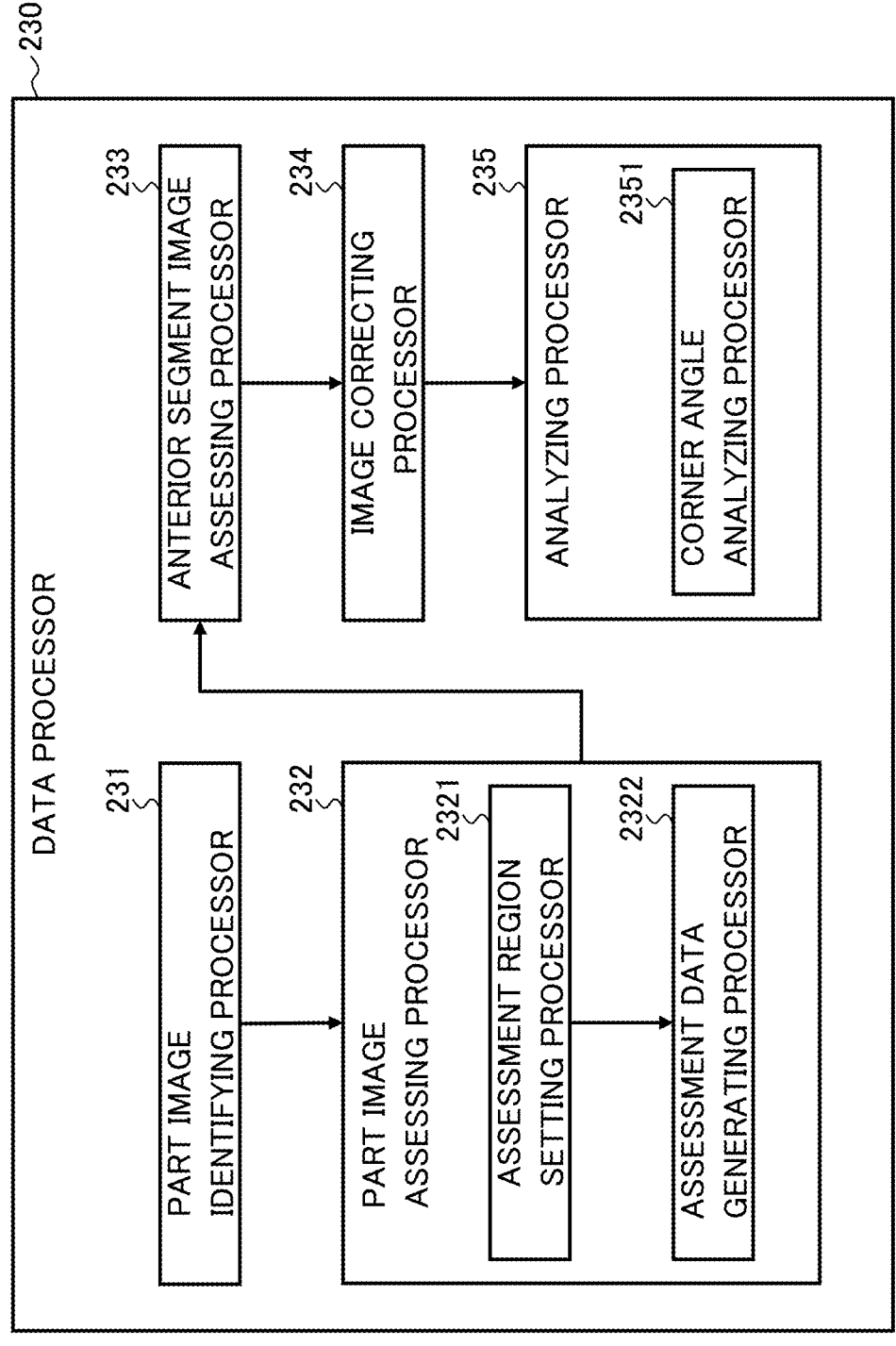
FIG. 4 is a diagram of an example of a configuration of an ophthalmic apparatus according to an aspect example.

FIG. 3 and FIG. 4 illustrate examples of the configurations of the control system and the processing system of the ophthalmic apparatus 1. The arithmetic and control unit 200 of some examples may include the controller 210, the image data constructing unit 220, and the data processor 230. The ophthalmic apparatus 1 may further include a communication device for performing data communication with external apparatuses. The ophthalmic apparatus 1 may further include a drive device (reader and/or writer) for reading out data from recording media and writing data into recording media.

<Controller 210>

The controller 210 performs various kinds of controls. The controller 210 includes the main controller 211 and the memory 212. The main controller 211 includes one or more processors and executes control of each element of the ophthalmic apparatus 1 (including the elements shown in FIG. 1 to FIG. 4). The main controller 211 is implemented by cooperation between hardware including the one or more processors and control software.

The photography focus driver 31A is configured to move the photography focusing lens 31 disposed in the photographing optical path and the focusing optical system 60 disposed in the illumination optical path under control of the main controller 211. The retroreflector driver (RR driver) 41A is configured to move the retroreflector 41 disposed in the sample arm under control of the main controller 211. The OCT focus driver 43A is configured to move the OCT focusing lens 43 disposed in the sample arm under control of the main controller 211. The retroreflector driver (RR driver) 114A is configured to move the retroreflector 114 disposed in the reference arm under control of the main controller 211. Each of the above drivers includes an actuator, such as a pulse motor, that operates under control of the main controller 211. The optical scanner 44 disposed in the sample arm also operates under control of the main controller 211.

The movement mechanism 150 of some examples is configured to move the fundus camera unit 2 in a three dimensional manner. The movement mechanism 150 of some typical examples includes the following elements: an x stage that is movable in the ±x directions (left and right directions); an x movement mechanism configured to move the x stage; a y stage that is movable in the ±y directions (upward and downward directions); a y movement mechanism configured to move the y stage; a z stage that is movable in the ±z directions (front and back directions, depth direction); and a z movement mechanism configured to move the z stage. Each of these movement mechanisms includes an actuator, such as a pulse motor, that operates under control of the main controller 211.

The insertion and removal mechanism 400A is configured to perform an operation of inserting the anterior segment OCT attachment 400 into the OCT optical path (the sample arm), and an operation of removing the anterior segment OCT attachment 400 from the sample arm. The insertion and removal mechanism 400A includes an actuator, such as a solenoid actuator, that operates under control of the main controller 211.

The memory 212 retains various kinds of data. Examples of data stored in the memory 212 include OCT images, digital images (anterior segment images, fundus images), subject's eye information, and analysis data. The subject's eye information includes subject information such as a patient identifier (patient ID) and a patient's name, identification information for right and left eyes, and electronic medical record information.

<Image Data Constructing Unit 220>

The image data constructing unit 220 includes one or more processors and is configured to construct OCT image data of the subject's eye E based on signals (sampling data) input from the data acquisition system 130. The OCT image data constructed by the image data constructing unit 220 is one or more pieces of A-scan image data, and typically is B-scan image data (two dimensional cross sectional image data, two dimensional tomographic image data) consisting of a plurality of pieces of A-scan image data.

The process of constructing OCT image data includes noise elimination (noise reduction), filtering, fast Fourier transform (FFT), and other processes, as in existing or conventional Fourier domain OCT techniques. In the cases in which other types of OCT techniques are employed, the image data constructing unit 220 executes known processing in accordance with an OCT technique employed.

The image data constructing unit 220 may be configured to construct three dimensional data of the subject's eye E based on signals input from the data acquisition system 130. This three dimensional data is three dimensional image data representing a three dimensional region (referred to as a volume) of the subject's eye E. This three dimensional image data is image data in which the positions of pixels are defined using a three dimensional coordinate system. Examples of such three dimensional image data include stack data and volume data.

Stack data is image data formed by arranging (disposing), in a three dimensional manner, a plurality of cross sectional images acquired along a plurality of scan lines, on the basis of the positional relationship between these scan lines. In other words, stack data is image data constructed by representing multiple cross sectional images, which are originally defined in individually different two dimensional coordinate systems, with a single three dimensional coordinate system, that is, by embedding the multiple cross sectional images into a single three dimensional space. In further other words, stack data is image data formed by arranging, in a three dimensional manner, a plurality of pieces of A-scan image data acquired respectively for a plurality of scan points arranged in a two dimensional manner (that is, for a scan point array), on the basis of the positional relationship between these scan points.

Volume data is image data whose elements (picture elements) are voxels arranged in a three dimensional manner. Volume data is also referred to as voxel data. volume data is constructed by applying processing such as interpolation and voxelization to stack data.

The image data constructing unit 220 constructs an image for display, by applying rendering to three dimensional image data. Examples of applicable rendering techniques include volume rendering, surface rendering, maximum intensity projection (MIP), minimum intensity projection (MinIP), and multi planar reconstruction (MPR).

The image data constructing unit 220 may be configured to construct an OCT front image (OCT en face image) based on three dimensional image data. The image data constructing unit 220 of some examples may be configured to construct projection data of three dimensional image data by applying, to the three dimensional image data, projection processing in the z direction (A-line direction, depth direction). Similarly, the image data constructing unit 220 may be configured to construct projection data from partial data of three dimensional image data such as a slab of three dimensional image.

In some typical examples, partial data of three dimensional image data, such as a slab, may be obtained by using segmentation processing. Segmentation, or image segmentation, is image processing of partitioning an image to identify a partial region. Segmentation of some typical examples is performed to identify an image region corresponding to a predetermined tissue of the subject's eye E. Segmentation of some examples may include any known image processing techniques, and may include, for example, image processing such as edge detection and/or a segmentation technique using machine learning (e.g., deep learning). Segmentation of the present aspect example is executed, for example, by the image data constructing unit 220 or the data processor 230.

The ophthalmic apparatus 1 may be capable of performing OCT motion contrast imaging. OCT motion contrast imaging is a technique of imaging motion of fluid (liquid) etc. in an eye (see, for example, Japanese Unexamined Patent Application Publication (Translation of PCT Application) No. 2015-515894).

The image data constructing unit 220 is implemented by cooperation between hardware including one or more processors and image data constructing software.

<Data Processor 230>

The data processor 230 includes one or more processors and is configured to perform predetemined data processing on an image of the subject's eye E. The data processor 230 of some examples is implemented by cooperation between hardware including the one or more processors and data processing software.

The data processor 230 may be configured to perform position matching (registration) between two images acquired for the subject's eye E. The data processor 230 of some examples may be configured to perform registration between three dimensional image data acquired using OCT scanning and a front image (en face image) acquired by the fundus camera unit 2. The data processor 230 of some examples may be configured to perform registration between two OCT images acquired using OCT scanning. The data processor 230 of some examples may be configured to perform registration between two front images acquired by the fundus camera unit 2. The data processor 230 of some examples may be configured to apply registration to any of resulting data of analysis of one or more OCT images, resulting data of analysis of one or more front images, and other analysis results. Registration may be performed using freely selected known techniques. Registration of some examples may include feature point extraction and affine transformation.

The data processor 230 of some aspect examples, as shown in FIG. 4, may include the part image identifying processor 231, the part image assessing processor 232, the anterior segment image assessing processor 233, the image correcting processor 234, and the analyzing processor 235. In some aspect examples, the part image assessing processor 232 may include the assessment region setting processor 2321, and the assessment data generating processor 2322. In some aspect examples, the analyzing processor 235 may include the corner angle analyzing processor 2351.

As mentioned above, the data processor 230 may process the anterior segment image acquired by applying OCT scanning to the anterior segment Ea. Aspects (modes, types, etc.) of an anterior segment image processed by the data processor 230 are freely selected or designed. For example, an area or region to which OCT scanning is applied (scan size), a pattern of OCT scanning (scan pattern), and any other scan parameters may be freely selected or designed. The scan size may be defined by scan length, scan area (quantity that expresses the extent of a two dimensional region to which OCT scanning is applied), scan volume (quantity that expresses the extent of a three dimensional region to which OCT scanning is applied), scan angle (angle of view of OCT scanning), field of view, or other scan parameters. The scan pattern may be any of B-scan (line scan), circle scan, radial scan, volume scan (three dimensional scan), or other patterns.

The present disclosure gives descriptions of aspect examples of anterior segment images obtained by wide angle B-scans (wide angle images) and descriptions of aspect examples of anterior segment images obtained by non-wide angle B-scans (non-wide angle images); however, embodiments are not limited to these aspect examples. For example, a wide angle image may be an anterior segment image acquired by applying an OCT scan of a scan size equal to or larger than a predetermined value to the anterior segment Ea, and a non-wide angle image may be an anterior segment image acquired by applying an OCT scan of a scan size smaller than this predetermined value to the anterior segment Ea. In the present disclosure, "wide angle" and "non-wide angle" may not be distinguished by a certain absolute criterion (absolute standard, absolute basis, absolute reference, or the like), but they may be relative to each other. A B-scan applied to an anterior segment in some aspect examples may be defined to be a wide angle B-scan if the length of this B-scan is equal to or greater than a standard (typical) corneal diameter (vertical diameter, horizontal diameter (white-to-white)) while a B-scan may be defined to be a non-wide angle B-scan if the length of this B-scan is smaller than this standard corneal diameter.

Figure 5A:
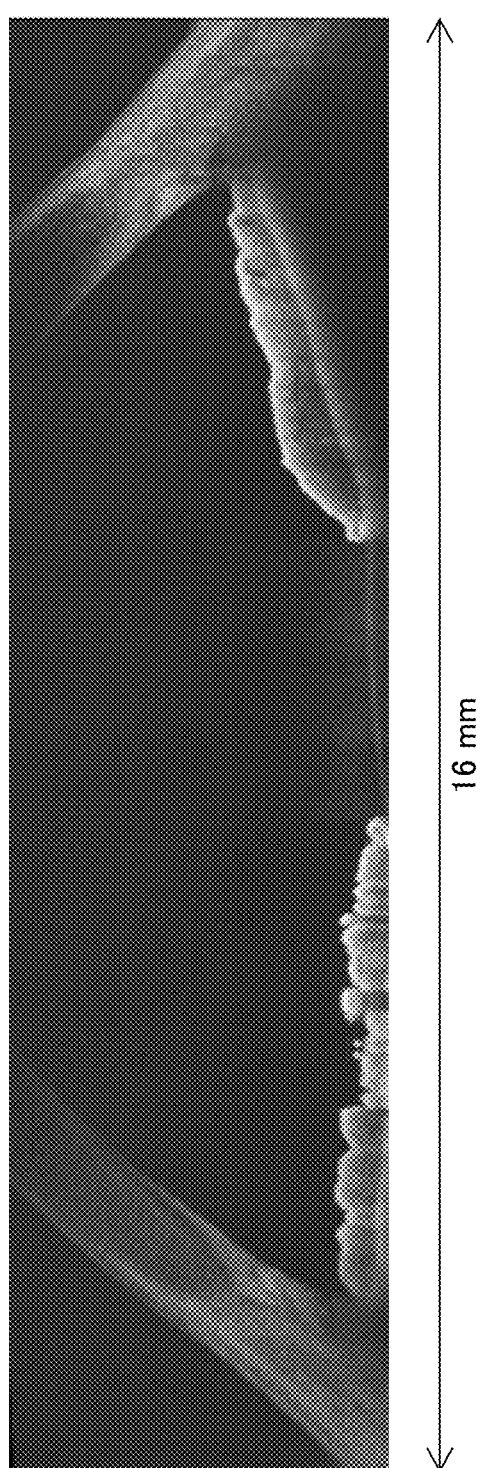
FIG. 5A is a diagram illustrating an example of processing executed by an ophthalmic apparatus according to an aspect example.

As a specific example, a wide angle image is acquired by applying, to the anterior segment Ea, a B-scan with the scan length of 16 mm. The scan line of this wide angle B-scan crosses (intersects) the corner angle of the anterior segment Ea twice. In typical examples, the scan line of this wide angle B-scan passes through the center of pupil (or its vicinity) of the anterior segment Ea and crosses the corner angle twice. FIG. 5A shows an example of a wide angle image obtained by this wide angle B-scan. The anterior segment image (wide angle image) of the present example does not provide an image (representation) of the entire anterior segment Ea, and an image corresponding to a central part (the corneal apex and its neighborhood) of the cornea is missing. It should be noted that a wide angle image of the entire cornea can be obtained in the case in which the imaging range and the scan area in the depth direction (z direction) are increased or in the case in which two or more times of OCT scans are executed with different coherence gates in the z direction.

Figure 5B:
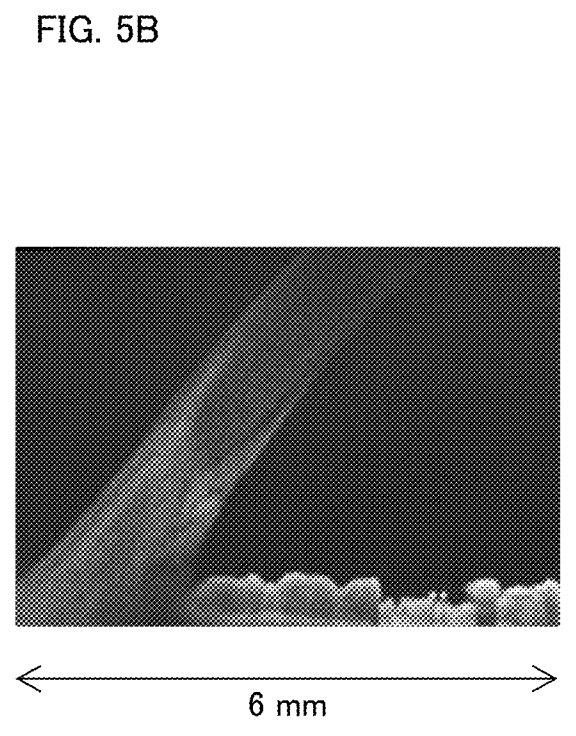

As a specific example, a non-wide angle image is acquired by applying, to the anterior segment Ea, a B-scan with the scan length of 6 mm. The scan line of this non-wide angle B-scan crosses the corner angle of the anterior segment Ea only once. FIG. 5B shows an example of a non-wide angle image obtained by this non-wide angle B-scan.

<Part Image Identifying Processor 231>

The part image identifying processor 231 is configured to identify two or more images respectively corresponding to two or more parts (sites, tissues, etc.) of the anterior segment Ea, from an anterior segment image acquired by applying OCT scanning to the anterior segment Ea. The two or more images identified are regions in the anterior segment image.

In the present disclosure, an image identified by the part image identifying processor 231, that is, an image corresponding to a predetermined site of an anterior segment, is referred to as a part image. The part image identifying processor 231 is implemented by cooperation between hardware including one or more processors and part image identifying software.

In some aspect examples, a part of an anterior segment to be detected as a part image from an anterior segment image, is set (determined, designated, selected) in advance. Examples of a part to be detected as a part image from an anterior segment image, include cornea (a part thereof), iris (a part thereof), anterior chamber (a part thereof), pupil (a part thereof), crystalline lens (a part thereof), and other parts of an eye.

The part image identifying processor 231 of some examples may be configured to perform identification of a part image by applying segmentation to an anterior segment image. For example, this segmentation may be executed to identify a region in an anterior segment image that corresponds to a predetermined part of the anterior segment Ea. This segmentation may include freely selected known image processing technique or technology. For example, this segmentation may include image processing such as edge detection and/or segmentation processing using machine learning such as deep learning. Some examples of processing that may be executed by the part image identifying processor 231 will be described below.

In some aspect examples, the part image identifying processor 231 may be configured to identify mutually different part image groups (mutually different sets of two or more part images) depending on the case in which an anterior segment image is a wide angle image or the case in which an anterior segment image is a non-wide angle image. Here, a part image group identified from a wide angle image is referred to as a first part image group, and a part image group identified from a non-wide angle image is referred to as a second part image group. The number of part images included in a first part image group and the number of part images included in a second part image group may be different from each other. Also, two or more parts of an anterior segment corresponding to a first part image group and two or more parts of an anterior segment corresponding to a second part image group may be different from each other.

Figure 6A:
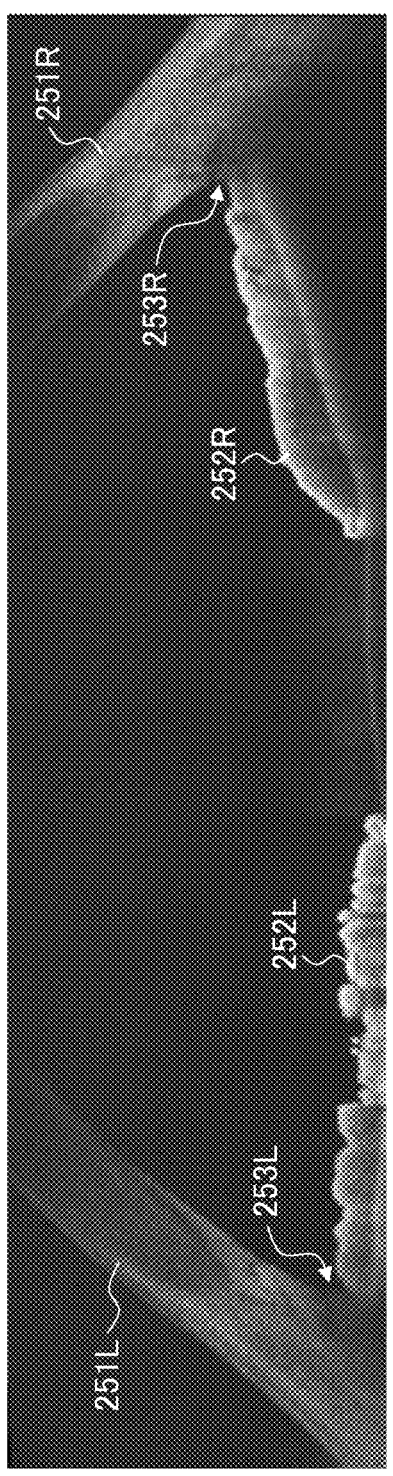
FIG. 6A is a diagram illustrating an example of processing executed by an ophthalmic apparatus according to an aspect example.

In some aspect examples, in the case in which the wide angle image shown in FIG. 6A is obtained, the part image identifying processor 231 may identify the following images from this wide angle image: an image of cornea (first cornea image) 251L that is located in the vicinity of a first frame edge (e.g., the left edge of the frame) of this wide angle image; and an image of cornea (second cornea image) 251R that is located in the vicinity of a second frame edge (e.g., the right edge of the frame) opposite to the first frame edge. Further, the part image identifying processor 231 may identify the following images: an image of iris (first iris image) 252L that is located in the vicinity of the first frame edge; and an image of iris (second iris image) 252R that is located in the vicinity of the second frame edge. In addition, the position of intersection between the first cornea image 251L and the first iris image 252L corresponds to the corner angle 253L, and the position of intersection between the second cornea image 251R and the second iris image 252R corresponds to the corner angle 253R.

Figure 6B:
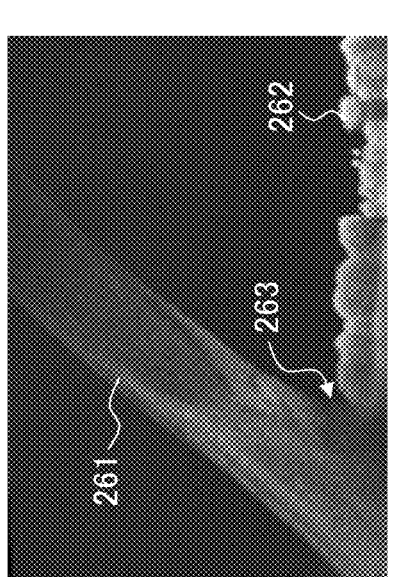
FIG. 6B is a diagram illustrating an example of processing executed by an ophthalmic apparatus according to an aspect example.

In some aspect examples, in the case in which the non-wide angle image shown in FIG. 6B is obtained, the part image identifying processor 231 may identify the single corneal image 261 and the single iris image 262 from this non-wide angle image. Here, the position of intersection between the cornea image 261 and the iris image 262 corresponds to the corner angle 263.

In some aspect examples, the part image identifying processor 231 may be configured to identify a part image by applying the above-mentioned edge detection to an anterior segment image. For example, in the case in which the wide angle image shown in FIG. 6A is obtained, the part image identifying processor 231 may identify the cornea images 251L and 251R and the iris images 252L and 252R by applying at least edge detection to this wide angle image. Also, in the case in which the non-wide angle image shown in FIG. 6B is obtained, for example, the part image identifying processor 231 may identify the cornea image 261 and the iris image 262 by applying at least edge detection to this non-wide angle image.

Further, in some aspect examples, the part image identifying processor 231 may be configured to apply edge detection to an anterior segment image (e.g., wide angle image or non-wide angle image), thereby identifying an image corresponding to an anterior surface of cornea (anterior corneal surface image) and/or an image corresponding to a posterior surface of cornea (posterior corneal surface image), and an image corresponding to an anterior surface of iris (anterior iridic surface image). In addition, the part image identifying processor 231 may be configured to identify an image corresponding to cornea (cornea image) based on the identified anterior corneal surface image and/or the identified posterior corneal surface image, and to identify an image corresponding to iris (iris image) based on the identified anterior iridic surface image.

Figure 7A:
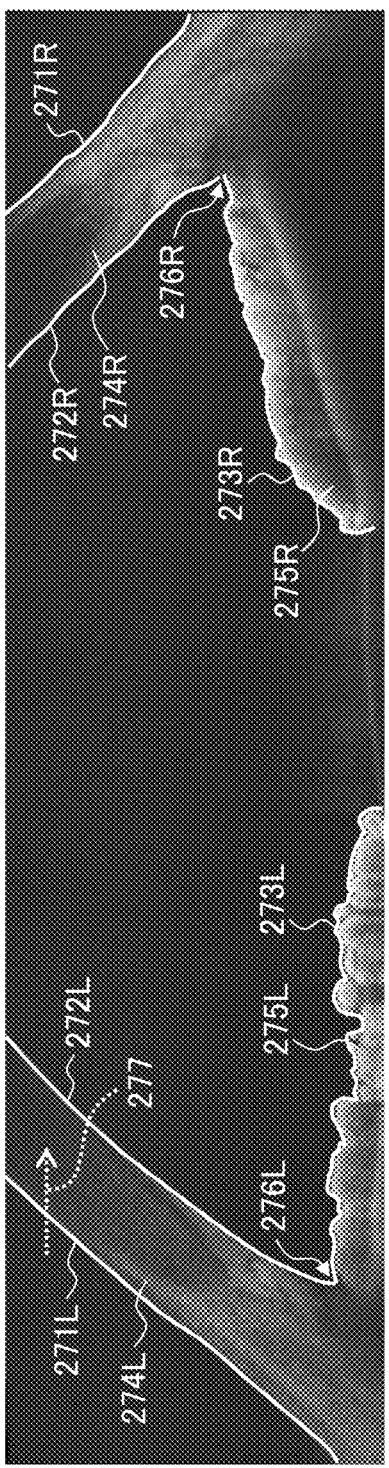
FIG. 7A is a diagram illustrating an example of processing executed by an ophthalmic apparatus according to an aspect example.

For example, in the case in which the wide angle image shown in FIG. 7A is obtained, the part image identifying processor 231 may apply edge detection to this wide angle image, thereby identifying the anterior corneal surface images 271 L and 271R, the posterior corneal surface images 272L and 272R, and the anterior iridic surface images 273L and 273R. Further, the part image identifying processor 231 may execute the following processes: a process of identifying the cornea image 274L whose boundary (outer edge, border) includes the anterior corneal surface image 271 L and the posterior corneal surface image 272L; a process of identifying the cornea image 274R whose boundary includes the anterior corneal surface image 271 R and the posterior corneal surface image 272R; a process of identifying the iris image 275L whose boundary includes the anterior iridic surface image 273L; and a process of identifying the iris image 275R whose boundary includes the anterior iridic surface image 273R.

Note that the position of intersection between the cornea image 274L and the iris image 275L corresponds to the corner angle 276L, and the position of intersection between the cornea image 274R and the iris image 275R corresponds to the corner angle 276R. In other words, the position of intersection between the posterior corneal surface image 272L and the anterior iridic surface image 273L corresponds to the corner angle 276L, and the position of intersection between the posterior corneal surface image 272R and the anterior iridic surface image 273R corresponds to the corner angle 276R.

In some aspect examples, the part image identifying processor 231 may be configured to identify an edge where a gradient direction is toward a frame edge of an anterior segment image (wide angle image) and where a gradient value is equal to or greater than a predetermined threshold value, in order to perform identification of the anterior corneal surface images 271 L and 271 R.

In some aspect examples, the part image identifying processor 231 may be configured to identify an edge where a gradient direction is toward a central region of the frame of an anterior segment image (wide angle image) and where a gradient value is equal to or greater than a predetermined threshold value, in order to perform identification of the posterior corneal surface images 272L and 272R.

Similarly, the identification of the anterior iridic surface images 273L and 273R may be performed by edge detection on the basis of a gradient (gradient direction, gradient value). Note that, in typical examples, a gradient direction may be defined to be the direction of a normal (normal line, normal vector) to that gradient.

Figure 7B:
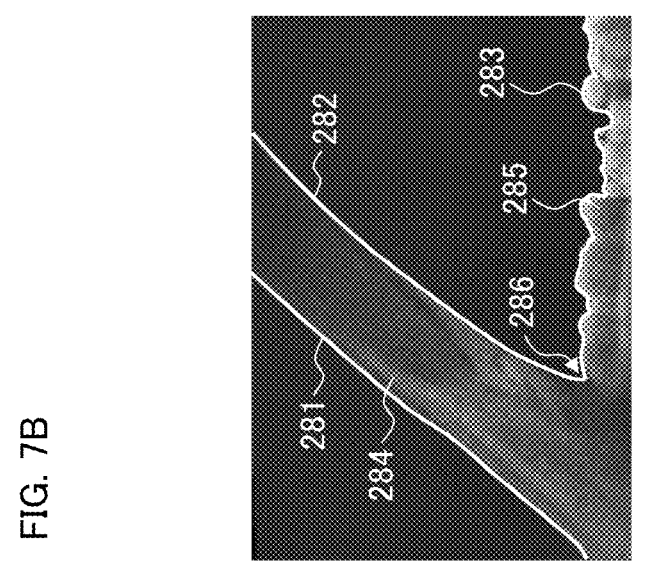

As another example, in the case in which the non-wide angle image shown in FIG. 7B is obtained, the part image identifying processor 231 may apply edge detection to this non-wide angle image, thereby identifying the anterior corneal surface image 281, the posterior corneal surface image 282, and the anterior iridic surface image 283. Similar to the case of a wide angle image described above, identification processes of these images 281, 282, and 283 may be performed by employing edge detection considering a gradient. Further, the part image identifying processor 231 may be configured to execute the following processes: a process of identifying the cornea image 284 whose boundary includes the anterior corneal surface image 281 and the posterior corneal surface image 282; and a process of identifying the iris image 285 whose boundary includes the anterior iridic surface image 283. Here, the position of intersection between the cornea image 284 and the iris image 285 corresponds to the corner angle 286. In other words, the position of intersection between the posterior corneal surface image 282 and the anterior iridic surface image 283 corresponds to the corner angle 286.

Figure 7C:
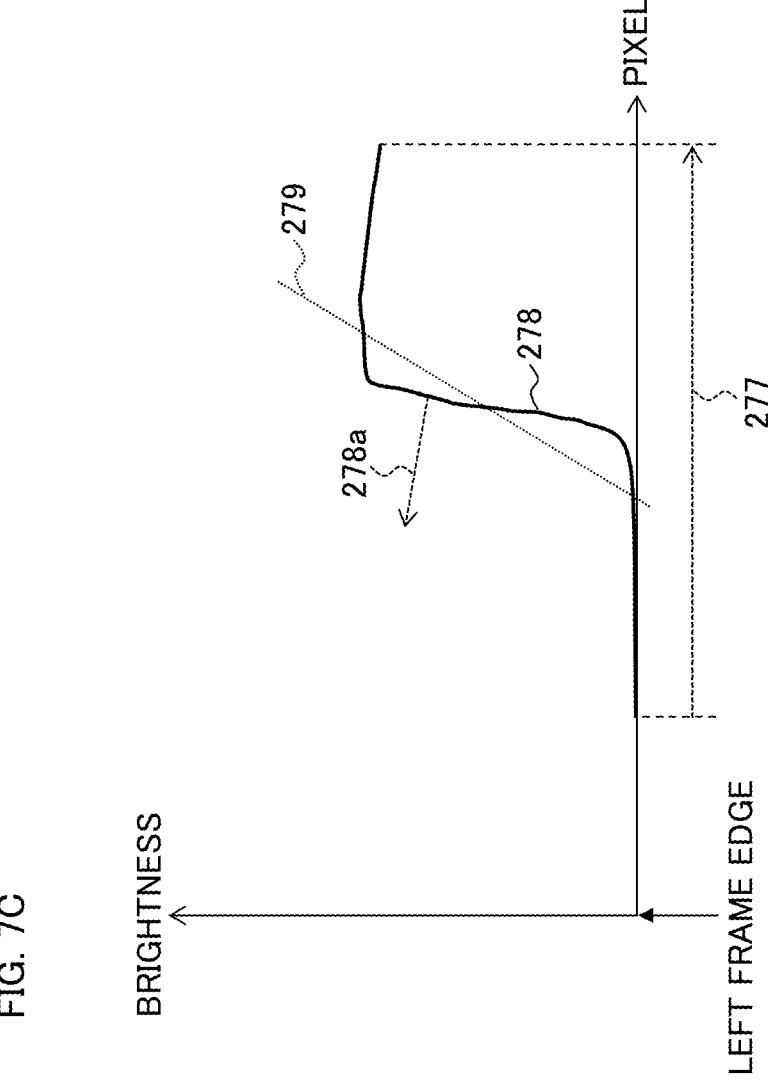
FIG. 7C is a diagram illustrating an example of processing executed by an ophthalmic apparatus according to an aspect example.

Edge detection for anterior corneal surface image identification will now be described in more details with further referring to FIG. 7C. As mentioned above, in some aspect examples, the part image identifying processor 231 may be configured to identify an anterior corneal surface image by identifying an edge where a gradient direction is toward a frame edge of an anterior segment image and where a gradient value is equal to or greater than a predetermined threshold value. The present example gives a description of the case in which the part image identifying processor 231 analyzes the one dimensional region 277 shown in FIG. 7A. The one dimensional region 277 consists of a plurality of pixels arranged in a line (see also FIG. 7C). The reference character 278 in FIG. 7C indicates a brightness distribution graph for the plurality of pixels arranged in the one dimensional region 277. As can be seen from the shape of the brightness distribution graph 278, a portion of the brightness distribution graph 278 meets the following conditions: a condition that the gradient value of brightness is greater than the predetermined threshold value 279; and a condition that the normal direction (normal vector) 278a that indicates the direction of the gradient is toward the left frame edge (the left edge of the frame). A region with such gradients is detected as an edge. Applying such processing to various one dimensional regions allows the anterior corneal surface image 271 L to be identified. Similarly, the anterior corneal surface image 271 R can be identified by searching a portion of the brightness distribution graph where the gradient value of brightness is greater than a predetermined threshold value and the normal direction that indicates the direction of the gradient is toward the right frame edge (the right edge of the frame).

In the same way, the part image identifying processor 231 can identify the posterior corneal surface images 272L and 272R by detecting an edge where a gradient direction is toward a central region of the frame of an anterior segment image (wide angle image) and where a gradient value is equal to or greater than a predetermined threshold value.

<Part Image Assessing Processor 232>

The part image assessing processor 232 is configured to assess image quality of each of the two or more part images identified by the part image identifying processor 231. The part image assessing processor 232 may be configured to perform image quality assessment using freely selected known techniques. The part image assessing processor 232 is implemented by cooperation between hardware including one or more processors and part image assessing software.

As mentioned above, the part image assessing processor 232 of some aspect examples may include the assessment region setting processor 2321 and the assessment data generating processor 2322.

<Assessment Region Setting Processor 2321>

The assessment region setting processor 2321 is configured to set an assessment region for each of the two or more part images identified by the part image identifying processor 231. The assessment region setting processor 2321 is implemented by cooperation between hardware including one or more processors and assessment region setting software.

In some aspect examples, the assessment region setting processor 2321 may be configured to set an assessment region for each of the two or more part images identified by the part image identifying processor 231 in such a manner that each assessment region includes a first region that is at least part of a corresponding part image and a second region that is located outside this corresponding part image. Further, the assessment region setting processor 2321 may be configured to set each assessment region in such a manner that the first region and the second region in that assessment region are adjacent to each other.

Figure 8A:
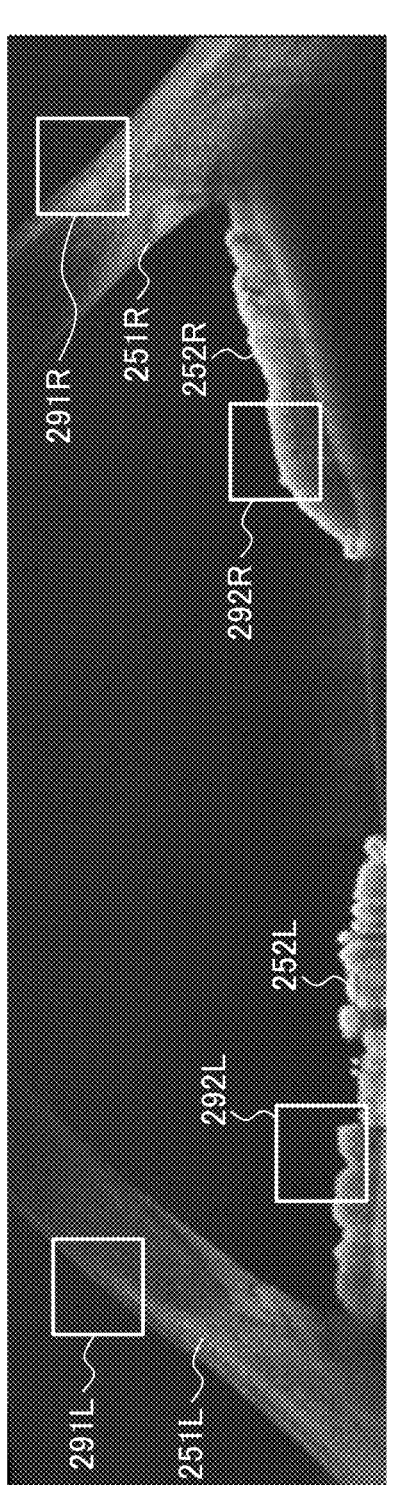
FIG. 8A is a diagram illustrating an example of processing executed by an ophthalmic apparatus according to an aspect example.

Some specific examples of processing of setting assessment regions will now be described. In a specific example, as shown in FIG. 6A, the cornea images 251L and 251R and the iris images 252L and 252R are identified from an anterior segment image (wide angle image). The assessment region setting processor 2321 may execute the following processes as shown in FIG. 8A: a process of setting the assessment region 291L for the cornea image 251L; a process of setting the assessment region 291R for the cornea image 251R, a process of setting the assessment region 292L for the iris image 252L; and a process of setting the assessment region 292R for the iris image 252R.

Note that the assessment region 291L includes both a partial region (corresponding to the first region) of the cornea image 251L and a region (corresponding to the second region) located outside the cornea image 251L (that is, located in a background region), and that this first region and this second region are adjacent to each other. In other words, the single assessment region 291L of a rectangular shape is arranged (designed) in such a manner as to include both an interior region and an exterior region of the cornea image 251L. Correspondingly, the assessment region 291R includes both a partial region (corresponding to the first region) of the cornea image 251R and a region (corresponding to the second region) located outside the cornea image 251R (that is, located in a background region).

Also, the assessment region 292L includes both a partial region (corresponding to the first region) of the iris image 252L and a region (corresponding to the second region) located outside the iris image 252L (that is, located in an anterior chamber image). In other words, the single assessment region 292L of a rectangular shape is arranged (designed) in such a manner as to include both an interior region and an exterior region of the iris image 252L. Correspondingly, the assessment region 292R includes both a partial region (corresponding to the first region) of the iris image 252R and a region (corresponding to the second region) located outside the iris image 252R (that is, located in an anterior chamber image).

Figure 8B:
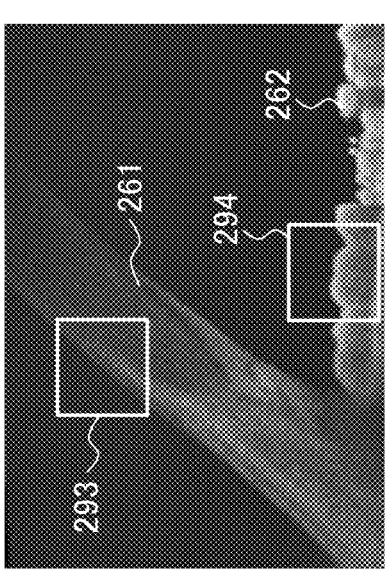
FIG. 8B is a diagram illustrating an example of processing executed by an ophthalmic apparatus according to an aspect example.

Another specific example will now be described. In the present example, as shown in FIG. 6B, the cornea image 261 and the iris image 262 are identified from an anterior segment image (non-wide angle image). The assessment region setting processor 2321 may execute the following processes as shown in FIG. 8B: a process of setting the assessment region 293 for the cornea image 261; and a process of setting the assessment region 294 for the iris image 262. The aspects of the assessment regions 293 and 294 may be the same as or similar to those of the assessment regions 291L and 292L shown in FIG. 8A, respectively.

Figure 8C:
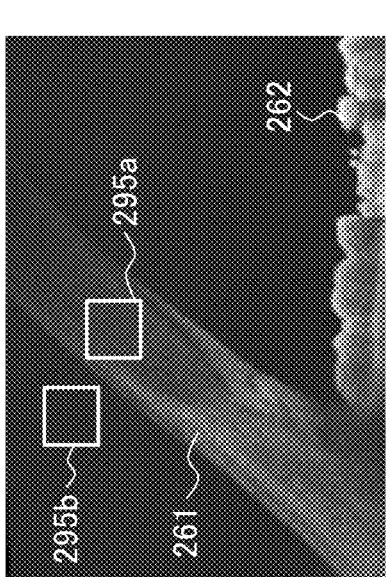
FIG. 8C is a diagram illustrating an example of processing executed by an ophthalmic apparatus according to an aspect example.

Yet another specific example will now be described. In the present example, as shown in FIG. 6B, the cornea image 261 and the iris image 262 are identified from an anterior segment image (non-wide angle image). The assessment region setting processor 2321 may set the two assessment regions 295a and 295b for the cornea image 261 as shown in FIG. 8C.

Note that the assessment region 295a is a partial region of the cornea image 261 and corresponds to an example of the first region mentioned above. Also note that the assessment region 295b is located (arranged) outside the cornea image 261 (that is, located in a background region) and corresponds to an example of the second region mentioned above. In the present example, the assessment region 295a (first region) and the assessment region 295b (second region) are not adjacent to each other. In other words, in the present example, the two rectangular-shaped assessment regions 295a and 295b are set in such a manner as to be apart from each other, and one of the two (the assessment region 295a in the present example) is a part of the cornea image 261 and the other (the assessment region 295b in the present example) is a part of the exterior region of the cornea image 261.

In some aspect examples, the number of assessment regions set for the cornea image 261 is not limited to two, and may be freely determined. That is, any number, two or more, of assessment regions may be set for the cornea image 261. The aspects (e.g., shapes, sizes) of an assessment region group (multiple assessment regions) set for the cornea image 261 may be the same or different. An assessment region group (multiple assessment regions) may be set for the iris image 262 in the same manner. Further, an assessment region group (multiple assessment regions) may be set in the same manner as in the case of processing a wide angle image like the image of FIG. 6A.

<Assessment Data Generating Processor 2322>

The assessment data generating processor 2322 is configured to analyze an assessment region set by the assessment region setting processor 2321, thereby generating assessment data that indicates (represents) the degree of image quality of a part image corresponding to this assessment region. In this way, the assessment data generating processor 2322 generates assessment data for each of the two or more part images identified by the part image identifying processor 231. That is, two or more pieces of assessment data corresponding to the two or more part images are obtained. The assessment data generating processor 2322 is implemented by cooperation between hardware including one or more processors and assessment data generating software.

Several examples of image quality assessment processing executed by the assessment data generating processor 2322 will now be described. In some aspect examples, image quality assessment processing executed by the assessment data generating processor 2322 may include freely selected or designed processing, and may include processing using any known technique and technology such as signal-to-noise ratio (SNR), contrast-to-noise ratio (CNR), root mean square granularity (RMS granularity), Wiener spectrum, modulation transfer function (MTF), quality index (QI) as described in Japanese Patent No. 6023406.

The assessment data generating processor 2322 of some examples may be configured to obtain assessment data of a part image by calculating a value of a predetermined image quality assessment indicator (image quality assessment index, image quality assessment parameter). The image quality assessment indicator is referred to as an image quality assessment value. The image quality assessment value may be a freely selected or designed parameter that represents a quantitative quality of an OCT image. In some typical examples, the higher the quality of an OCT image, the greater the magnitude of the image quality assessment value.

An example of a method of calculating an image quality assessment value will now be described. This example gives a method of calculating a known image quality value (IQ value). To begin with, the assessment data generating processor 2322 applies a predetermined analysis processing (e.g., segmentation) to an assessment region set for a part image, thereby detecting a tissue image region and a non-tissue image region. Here, the tissue image region is an image region corresponding to a tissue (site, part, etc.) of an anterior eye segment, and the non-tissue image region is an image region other than the tissue image region. Next, the assessment data generating processor 2322 creates a brightness histogram of the tissue image region and a brightness histogram of the non-tissue image region. Next, the assessment data generating processor 2322 calculates an image quality assessment value based on the degree of overlap between these two brightness histograms. For example, the image quality assessment value is defined in the range [0, 100] in such a manner that the image quality assessment value is zero if the two brightness histograms exactly (completely, fully, wholly) overlap (match, coincide) each other and that the image quality assessment value is 100 if the two brightness histograms are completely separate from each other. The image quality calculation of the present example may include any processes such as normalization of the two histograms, generation of a probability distribution function, calculation of an IQ value on the basis of a predetermined arithmetic expression.

A specific example will now be described. The present example considers the case, as shown in FIG. 8A, in which the assessment regions (referred to as cornea assessment regions) 291L and 291R are set for the cornea images 251L and 251R, respectively, and, the assessment regions (referred to as iris assessment regions) 292L and 292R are set for the iris images 252L and 252R, respectively. Then, the assessment data generating processor 2322 may perform the following processes: a process of generating assessment data of the cornea image 251L by analyzing the cornea assessment region 291L; a process of generating assessment data of the cornea image 251R by analyzing the cornea assessment region 291R; a process of generating assessment data of the iris image 252L by analyzing the iris assessment region 292L; and a process of generating assessment data of the iris image 252R by analyzing the iris assessment region 292R. Assessment data of a cornea image is referred to as cornea assessment data, and assessment data of an iris image is referred to as iris assessment data.

Another specific example will now be described. The present example considers the case, as shown in FIG. 8B, in which the assessment region (cornea assessment region) 293 is set for the cornea image 261, and, the assessment region (iris assessment region) 294 is set for the iris image 262. Then, the assessment data generating processor 2322 may perform the following processes: a process of generating assessment data (cornea assessment data) of the cornea image 261 by analyzing the cornea assessment region 293; and a process of generating assessment data (iris assessment data) of the iris image 262 by analyzing the iris assessment region 294.

Yet another specific example will now be described. The present example considers the case, as shown in FIG. 8C, in which the two assessment regions (cornea assessment regions) 295a and 295b are set for the cornea image 261. Then, the assessment data generating processor 2322 may perform a process of generating assessment data (cornea assessment data) of the cornea image 261 by analyzing the cornea assessment region consisting of the two cornea assessment regions 295a and 295b. This assessment data generation processing may include the following processes, for example: a process of generating, from the cornea assessment region 295a, a brightness histogram of a tissue image region as described above; and a process of generating, from the cornea assessment region 295b, a brightness histogram of a non-tissue image region as described above. Processes other than these two histogram generation processes in the assessment data generation processing of the present example, may be executed in the same manner as any known IQ value calculation processing mentioned above.

In the case in which three or more assessment regions are set for a cornea image, the assessment data generating processor 2322 may first classify (sort, categorize) the three or more assessment regions into an assessment region group corresponding to tissue image regions and another assessment region group corresponding to non-tissue image regions. Further, the assessment data generating processor 2322 may perform a process of generating one or more brightness histograms from the assessment region group corresponding to tissue image regions, and a process of generating one or more brightness histograms from the assessment region group corresponding to non-tissue image regions. Processes other than these two histogram generation processes in the assessment data generation processing of the present example, may be executed in the same manner as any known IQ value calculation processing mentioned above.

In the case in which two or more assessment regions are set for an iris image, the assessment data generating processor 2322 may also execute similar processing to generate iris assessment data.

<Anterior Segment Image Assessing Processor 233>

The anterior segment image assessing processor 233 is configured to assess the image quality of an anterior segment image based on two or more pieces of assessment data obtained for two or more part images by the part image assessing processor 232. The anterior segment image assessing processor 233 is implemented by cooperation between hardware including one or more processors and anterior segment image assessing software.

Processing executed by the anterior segment image assessing processor 233 may be freely selected or designed. That is, the anterior segment image assessing processor 233 performs anterior segment image assessment by applying freely selected or designed processing to two or more pieces of assessment data obtained for two or more part images by the part image assessing processor 232.

In some aspect examples, the anterior segment image assessing processor 233 may be configured, in order to perform assessment of an image quality of an anterior segment image, to apply predetermined statistical calculation (statistical operation) to two or more pieces of assessment data obtained for two or more part images by the part image assessing processor 232. This statistical calculation may include a freely selected or designed statistical calculation or statistical operation (a freely selected or designed statistical algorithm) such as one or more of average calculation (averaging calculation), variance calculation, standard deviation calculation, median calculation, maximum value calculation, minimum value calculation, mode calculation, comparison operation, and ordering operation (sequencing operation).

The anterior segment image assessing processor 233 may perform assessment of the image quality of an anterior segment image based on a quantity or a value (statistic) derived using the statistical calculation (statistical operation). The anterior segment image assessing processor 233 of some examples may be configured to perform the assessment of the image quality of an anterior segment image by executing a process of comparing a calculated statistic with a predetermined threshold value or a process of judging whether or not a calculated statistic belongs to a predetermined range. For example, in the case in which assessment data obtained by the part image assessing processor 232 includes an IQ value described above, the anterior segment image assessing processor 233 may be configured to execute the following processes: a process of comparing a statistic calculated by applying a predetermined statistical calculation to two or more IQ values, with a predetermined threshold value (minimum permissible level); a process of determining that the image quality of an anterior segment image is satisfactory (good, fine, sufficient, etc.) if the calculated statistic is equal to or greater than the threshold value; and a process of determining that the image quality of the anterior segment image is unsatisfactory (bad, poor, insufficient, etc.) if the calculated statistic is smaller than the threshold value.

In some aspect examples, the anterior segment image assessing processor 233 may perform image quality assessment by applying averaging calculation to two or more pieces of assessment data obtained for two or more part images by the part image assessing processor 232.

For example, in the case in which the part image assessing processor 232 is configured to generate cornea assessment data and iris assessment data, and in which the cornea assessment data includes an IQ value and the iris assessment data includes an IQ value, the anterior segment image assessing processor 233 may be configured to execute the following processes: a process of calculating the mean value of the IQ value in the cornea assessment data and the IQ value in the iris assessment data; a process of determining that the image quality of an anterior segment image is satisfactory if the calculated mean value is equal to or greater than a threshold value; and a process of determining that the image quality of the anterior segment image is unsatisfactory if the calculated mean value is smaller than the threshold value.

In some aspect examples, the anterior segment image assessing processor 233 may be configured to perform assessment of the image quality of an anterior segment image, at least by executing a process of comparing two or more pieces of assessment data obtained for two or more part images by the part image assessing processor 232 to select assessment data corresponding to the lowest image quality from the two or more pieces of assessment data.

For example, in the case in which the part image assessing processor 232 is configured to generate cornea assessment data and iris assessment data, and in which the cornea assessment data includes an IQ value and the iris assessment data includes an IQ value, the anterior segment image assessing processor 233 may be configured to execute the following processes: a process of comparing the IQ value in the cornea assessment data and the IQ value in the iris assessment data with each other to select assessment data corresponding to the lower (lowest) IQ value of these two IQ values; a process of determining that the image quality of an anterior segment image is satisfactory if the IQ value of the selected assessment data is equal to or greater than a threshold value; and a process of determining that the image quality of the anterior segment image is unsatisfactory if the IQ value of the selected assessment data is smaller than the threshold value.

<Image Correcting Processor 234>

The image correcting processor 234 is configured to apply predetermined correction processing to an anterior segment image. The image correcting processor 234 is implemented by cooperation between hardware including one or more processors and image correcting software.

In some aspect examples, the image correcting processor 234 is configured to correct the pixel aspect ratio of an anterior segment image. The image data constructing unit 220 constructs an OCT image (anterior segment image, fundus image) of a predetermined pixel aspect ratio, from data acquired by OCT scanning.

Figure 9:
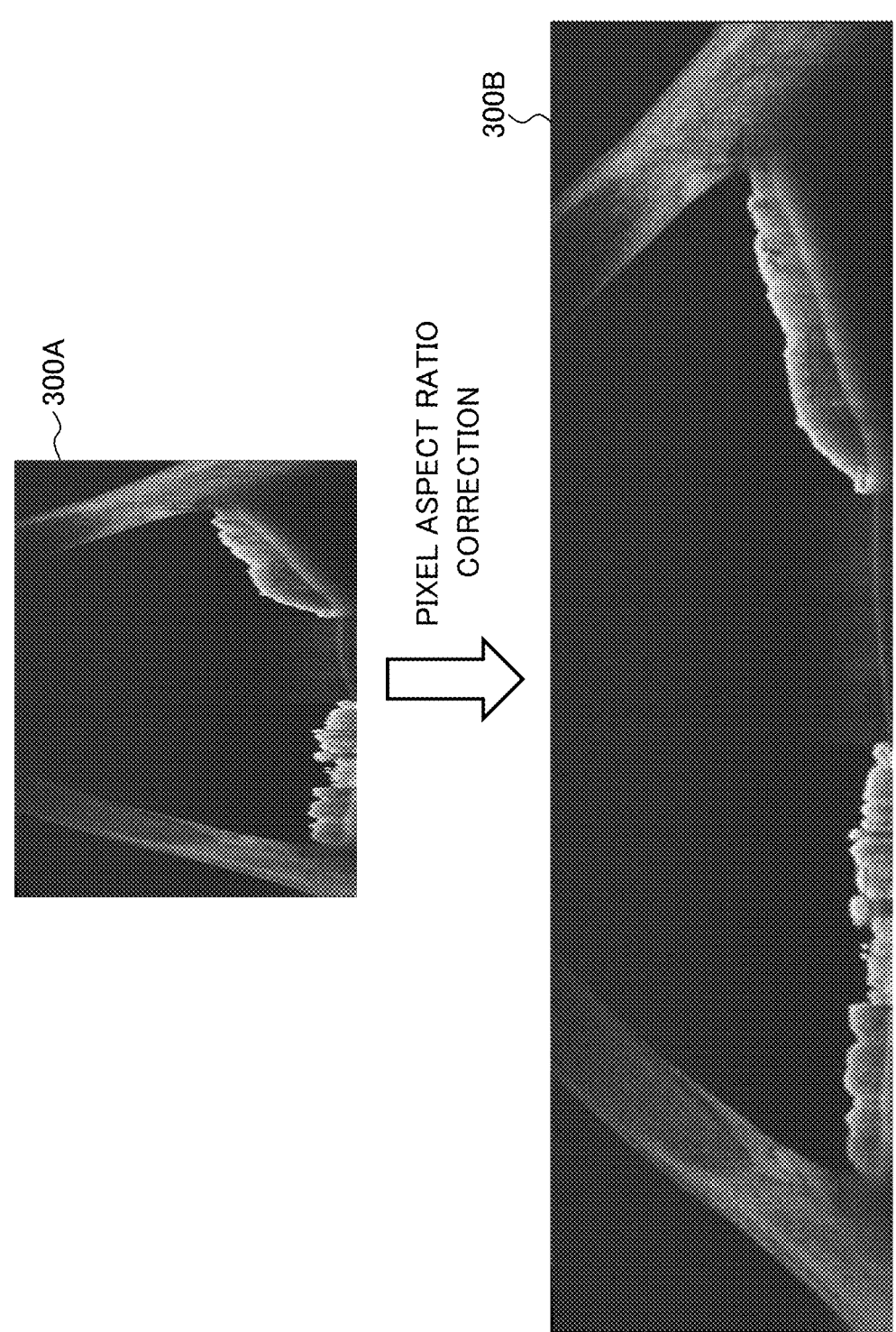
FIG. 9 is a diagram illustrating an example of processing executed by an ophthalmic apparatus according to an aspect example.

The image correcting processor 234 of some typical aspect examples is configured to convert (transform) this OCT image into an image of the pixel aspect ratio corresponding to the real space, that is, an image of the pixel aspect ratio 1:1. As shown in FIG. 9, for example, this pixel aspect ratio correction converts the anterior segment image 300A of the predetermined pixel aspect ratio constructed by the image data constructing unit 220 into the anterior segment image 300B of the pixel aspect ratio 1:1.

Execution of the pixel aspect ratio correction allows an anterior segment image that represents the actual morphology of an anterior segment to be obtained. In addition, analysis of this anterior segment image can generate analysis data that reflects the real states (real conditions) of the anterior segment such as the real scale and the real size of the anterior segment. Here, the analysis data includes, for example, one or more anterior segment parameters such as one or more corner angle parameters.

The image correcting processor 234 of the present example is configured to perform the pixel aspect ratio correction after the image quality assessment executed by the anterior segment image assessing processor 233, as shown in FIG. 4. However, in aspect examples, the stage in which and the timing at which pixel aspect ratio correction is performed may be freely selected. In some aspect examples, the timing of execution of pixel aspect ratio correction may be any of the followings: a time point after the anterior segment image construction executed by the image data constructing unit 220; a time point prior to the processing executed by the part image identifying processor 231; a time point after the processing executed by the part image identifying processor 231; a time point prior to the processing executed by the part image assessing processor 232; a time point prior to the processing executed by the assessment region setting processor 2321; a time point prior to the processing executed by the assessment data generating processor 2322; a time point after the processing executed by the assessment data generating processor 2322; a time point after the processing executed by the part image assessing processor 232; a time point prior to the processing executed by the anterior segment image assessing processor 233; and a time point after the processing executed by the anterior segment image assessing processor 233. In some typical examples, pixel aspect ratio correction is performed at a time point prior to the processing executed by the analyzing processor 235. Note that the data processor 230 of some aspect examples may be configured to apply correction processing equivalent to pixel aspect ratio correction, to analysis data derived by the analyzing processor 235.

Types of the image correction performed by the image correcting processor 234 are not limited to pixel aspect ratio correction. The image correcting processor 234 of some examples may apply, to an anterior segment, processing of correcting influence of refraction caused by a site (tissue, part) of an anterior segment (see, for example, PATENT DOCUMENTS 2 to 4 mentioned above). This processing is referred to as refraction correction. Refraction correction of some typical examples is used for correcting distortion of an anterior segment image caused by refraction at cornea (especially, at anterior surface of cornea).

There are cases in which an anterior segment image is obtained in which an image corresponding to a part of cornea (e.g., central part of cornea) is missing as shown in FIG. 5A. The image correcting processor 234 may be configured to estimate the shape of such a missing part by analyzing such an anterior segment image. This estimation processing may include the following processes, for example: a process of identifying left and right anterior corneal surface images from an anterior segment image (this process is described above); and a process of deriving an approximate curve of the anterior surface of the cornea (including the missing part) by applying curve fitting to the two anterior corneal surface images identified. This curve fitting may be any curve fitting on the basis of a robust estimation algorithm for removing an outlier, and more specifically, curve fitting on the basis of a random sample consensus (RANSAC) algorithm. By employing such a robust estimation algorithm, it becomes possible to remove an outlier(s) caused by noise or other factors, thereby performing curve fitting with a high degree of accuracy.

Further, the image correcting processor 234 may be configured to correct distortion of an anterior segment image based on the approximate curve obtained by the curve fitting (refraction correction).

<Analyzing Processor 235>

The analyzing processor 235 is configured to execute calculation of a predetermined anterior segment parameter(s) by analyzing an anterior segment image of the subject's eye E.

The analyzing processor 235 of some aspect examples may be configured to perform calculation of a predetermined anterior segment parameter by analyzing an anterior segment image to which at least the image distortion correction (refraction correction) described above has already been applied. With this configuration, it becomes possible to execute anterior segment parameter calculation with a high degree of accuracy and a high degree of precision based on an anterior segment image with distortion corrected.

Further, the analyzing processor 235 of some aspect examples may be configured to perform calculation of a predetermined anterior segment parameter by analyzing an anterior segment image to which the pixel aspect ratio correction described above has already been applied. With this configuration, it becomes possible to execute anterior segment parameter calculation with a high degree of accuracy and a high degree of precision based on an anterior segment image with pixel aspect ratio corrected. Note that the data processor 230 of the present example is configured to perform anterior segment analysis after predetermined image correction as shown in FIG. 4.

The anterior segment parameter(s) calculated by the analyzing processor 235 may be freely selected or designed. An anterior segment parameter is a value (quantity) representing the morphology (shape, form) of an anterior segment. Examples of anterior eye parameters include, in addition to corner angle parameters described later, radius of curvature of anterior corneal surface, radius of curvature of posterior corneal surface, radius of curvature of anterior surface of crystalline lens, radius of curvature of posterior surface of crystalline lens, corneal diameter (vertical diameter, horizontal diameter (white-to-white)), corneal thickness (central thickness, peripheral thickness), crystalline lens thickness, anterior chamber depth, anterior chamber volume, pupil diameter, and pupil center (eccentricity). The anterior segment parameter(s) calculated by the analyzing processor 235 may include shape distribution data, and may include, for example, corneal shape maps of various kinds such as a curvature map in the axial direction (axial curvature map), a tangential curvature map, an elevation map, a refractive power map, a thickness map (pachymetry map), a wavefront aberration map.

The methods and techniques of anterior segment parameter calculation may be freely selected or designed (see, for example, PATENT DOCUMENTS 1 to 4). In some typical examples, anterior segment parameter calculation may include the following processes: a process of identifying a predetermined site of an anterior segment, such as a process of segmentation, a process of feature point detection, or the like; and a measurement process such as one or more of distance measurement, area measurement, volume measurement, ratio calculation, and angle calculation.

The analyzing processor 235 is implemented by cooperation between hardware including one or more processors and analyzing software.

<Corner Angle Analyzing Processor 2351>

The analyzing processor 235 of the present example includes the corner angle analyzing processor 2351. The corner angle analyzing processor 2351 is configured to perform calculation of a predetermined corner angle parameter(s) by analyzing an anterior segment image. The corner angle analyzing processor 2351 of the present example is configured to perform calculation of a predetermined corner angle parameter by analyzing an anterior segment image whose pixel aspect ratio (and distortion) has been corrected by the image correcting processor 234.

A corner angle parameter is a parameter related to the site called corner angle (also referred to as angle of anterior chamber or anterior chamber angle) located between cornea and iris. Trabecular meshwork exists in corner angle. The magnitude of corner angle is considered to be one of determining factors of the flow speed of aqueous humor drained from an eyeball, and therefore one of determining factors of intraocular pressure. A corner angle parameter is used as an important index (important indicator, important information) for diagnosis of glaucoma, especially diagnosis of angle closure glaucoma.

Examples of a corner angle parameter include angle opening distance (AOD), anterior chamber angle (ACA), trabecular iris space area (TISA), angle recess area (ARA), and angle-to-angle distance (AtA) (see, for example, PATENT DOCUMENTS 1 to 3).

The methods and techniques of corner angle parameter calculation may be freely selected or designed (see, for example, PATENT DOCUMENTS 1 to 3). In some typical examples, corner angle parameter calculation may include the following processes: a process of identifying the position of corner angle or a predetermined position (location) in the vicinity of corner angle, such as a process of segmentation, a process of feature point detection, or the like; and a measurement process such as any of distance measurement, ratio calculation, and angle calculation.

The corner angle analyzing processor 2351 is implemented by cooperation between hardware including one or more processors and corner angle analyzing software.

<User Interface 240>

The user interface 240 includes the display device 241 and the operation device 242. The display device 241 includes the display device 3. The operation device 242 includes various operation devices and various input devices. The user interface 240 may include a device that has both a display function and an operation function, such as a touch panel. Some embodiment may not include at least part of the user interface 240. For example, a display device may be an external device or a peripheral device that is connected to the ophthalmic apparatus 1.

<Operation of Ophthalmic Apparatus>

Several examples of the operation of the ophthalmic apparatus 1 will be described. The same or similar preparatory processes as those performed by existing or conventional ophthalmic apparatuses, are performed before the operation described below. Examples of such preparatory processes may include a process of entering a patient identifier (ID), a process of inserting the anterior segment OCT attachment 400 into the sample arm, a process of presenting a fixation target to the subject's eye E, a process of adjusting fixation position, a process of alignment, a process of focus adjustment, and a process of OCT optical path length adjustment. FIG. 10 shows an example of the operation of the ophthalmic apparatus 1.

(S1: Acquire Anterior Segment Image)

To begin with, the ophthalmic apparatus 1 acquires an anterior segment image of the subject's eye E. In the present example, the ophthalmic apparatus 1 collects data from the anterior segment Ea by applying OCT scanning to the anterior segment Ea using the OCT scanner (the sample arm in the fundus camera unit 2, and the OCT unit 100, etc.), and constructs an anterior segment image from the collected data using the image data constructing unit 220. Suppose that the anterior segment image shown in FIG. 5B is obtained in the present example. The controller 210 sends the acquired anterior segment image to the data processor 230. The anterior segment image sent to the data processor 230 is input to the part image identifying processor 231.

(S2: Identify Two or more Part Images)

The part image identifying processor 231 identifies two or more part images respectively corresponding to two or more parts of the anterior segment Ea, from the anterior segment image acquired in the step S1. Suppose that, as shown in FIG. 6B, the cornea image 261 and the iris image 262 are identified from the anterior segment image of FIG. 5B in this the present example.

(S3: Set Assessment Region for Image Quality Assessment for each Part Image)

Next, the assessment region setting processor 2321 of the part image assessing processor 232 sets an assessment region for image quality assessment, for each part image identified in the step S2. Suppose that, as shown in FIG. 8B, the cornea assessment region 293 is set for the cornea image 261 and the iris assessment region 294 is set for the iris image 262 in the present example.

(S4: Generate Assessment Data for each Part Image)

Next, for each part image identified in the step S2, the assessment data generating processor 2322 of the part image assessing processor 232 generates assessment data for that part image by analyzing a corresponding assessment region set for that part image in the step S3. Suppose that assessment data (IQ value) of the cornea image 261 of FIG. 8B and assessment data (IQ value) of the iris image 262 of FIG. 8B are obtained in the present example.

(S5: Assess Image Quality of Anterior Segment Image)

Next, the anterior segment image assessing processor 233 performs assessment of the image quality of the anterior segment image acquired in the step 51, based on the two or more pieces of assessment data obtained for the two or more part images in the step S4.

(S6: Is Image Quality Satisfactory?)

If the image quality of the anterior segment image is assessed to be satisfactory in the step S5 (S6: Yes), the process moves on to the step S7.

On the other hand, if the image quality of the anterior segment image is assessed to be unsatisfactory in the step S5 (S6: No), the process moves back to the step S1. More specifically, in the case in which the image quality of the anterior segment image is assessed to be unsatisfactory in the present example, the ophthalmic apparatus 1 collects another data (new data) from the anterior segment Ea by applying OCT scanning again to the anterior segment Ea using the OCT scanner (data collector), and constructs another anterior segment image (new anterior segment image) from this newly acquired data using the image data constructing unit 220. Further, the ophthalmic apparatus 1 performs the processes of the steps S2 to S5 again based on this new anterior segment image. The series of processes of the steps S1 to S5 is repeated until a predetermined condition is met. This condition may be any one of the following conditions, for example: a condition that a judgement result "Yes" is obtained in the step S6; a condition that the number of times of the repetition reaches a predetermined number of times; and a condition that the time duration of the repetition reaches a predetermined time duration. Such repetitive scanning of the present example allows another anterior segment image of the anterior segment Ea to be automatically acquired in the case in which an anterior segment image with poor image quality is obtained.

(S7: Correct Anterior Segment Image)

Next, the image correcting processor 234 applies predetermined correction processing to the anterior segment image that has been assessed to have satisfactory image quality in the step S6. This correction processing may include one or more freely selected image corrections such as pixel aspect ratio correction and/or distortion correction (refraction correction).

(S8: Calculate Corner Angle Parameter)

Next, the corner angle analyzing processor 2351 of the analyzing processor 235 performs calculation of a predetermined corner angle parameter(s) by analyzing the anterior segment image to which the predetermined correction processing is applied in the step S7.

(S9: Display Anterior Segment Image and Corner Angle Parameter)

The main controller 211 displays, for example, the anterior segment image obtained in the step S7 and information on the corner angle parameter(s) obtained in the step S8, on the display device 241.

Figure 11A:
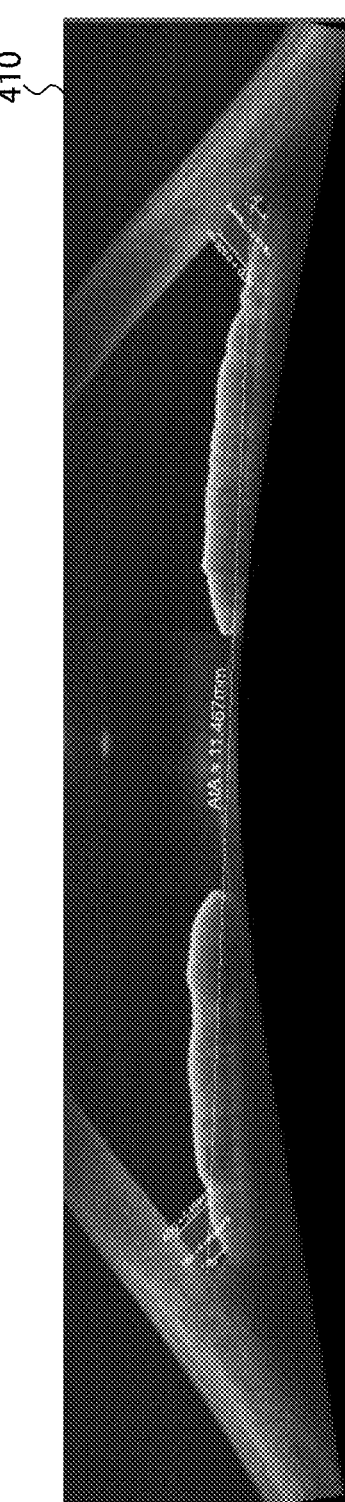
FIG. 11A is a diagram illustrating an example of an operation executed by an ophthalmic apparatus according to an aspect example.
Figure 11B:
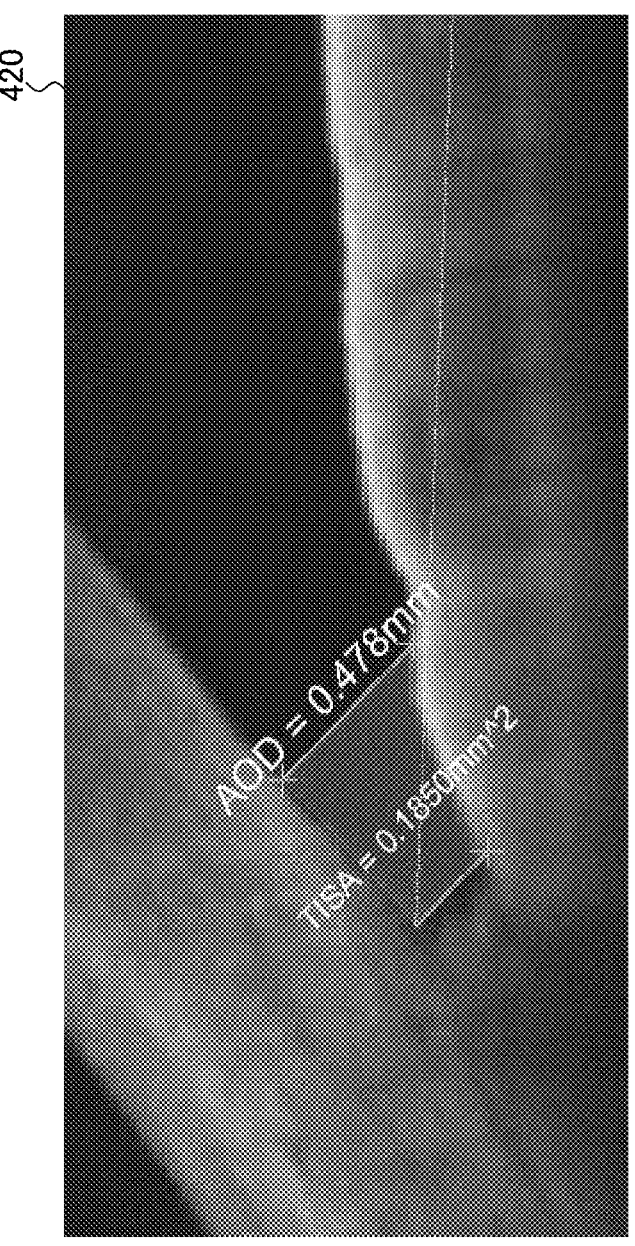
FIG. 11B is a diagram illustrating an example of an operation executed by an ophthalmic apparatus according to an aspect example.

Several examples of the information displayed in the step S9 are shown in FIG. 11A and FIG. 11B. The displayed information 410 shown in FIG. 11A presents, on the anterior segment image obtained in the step S7, the measurement positions and the measured values of the corner angle parameters (namely, AOD, TISA, and AtA) obtained in the step S8. The displayed information 420 shown in FIG. 11B shows an enlarged representation of a part of the displayed information 410 shown in FIG. 11A. The displayed information 420 presents the measurement positions and the measured values of the corner angle parameters (namely, AOD and TISA) obtained in the step S8, on the enlarged image of the corner angle and its vicinity in the anterior segment image obtained in the step S7.

(S10: Save anterior segment image and corner angle parameter)

The main controller 211 stores one or more anterior segment images of the subject's eye E and the information on the corner angle parameter obtained in the step S8 in, for example, the memory 212 and/or a storage device. The one or more anterior segment images stored may include, for example, either one or both of the anterior segment image obtained in the step S1 and the anterior segment image to which the correction processing has been applied in the step S5. This completes the present operation example (End).

<Modification Examples>

While the ophthalmic apparatus 1 described above includes the OCT scanner (data collector) and the image data constructing unit (image constructing processor), an ophthalmic apparatus of some aspect examples may not include either one or both of the OCT scanner and the image data constructing unit. For example, the ophthalmic apparatus 500 shown in FIG. 12 includes neither the OCT scanner nor the image data constructing unit, but includes the image receiver 530 in place of the OCT scanner and the image data constructing unit.

The image receiver 530 has the function of receiving an anterior segment image of a subject's eye from an external source. In some aspect examples, the image receiver 530 may include a communication device for performing data communication with external apparatuses, and may be configured to obtain an anterior segment image of a subject's eye from an external apparatus. In some aspect examples, the image receiver 530 may include a drive device for reading out data stored in a recording medium, and may be configured to obtain an anterior segment image of a subject's eye from a recording medium.

Thus, while the ophthalmic apparatus 1 described above constructs an OCT image by itself, the ophthalmic apparatus 500 of the present modification example obtains an OCT image from an external source. The ophthalmic apparatus 500 of the present modification example may be, for example, a single computer or two or more computers, and may typically be a personal computer or a server.

Similar to the ophthalmic apparatus 1 described above, the ophthalmic apparatus 500 includes the controller 510, the user interface 520, the part image identifying processor 540, the part image assessing processor 550, the anterior segment image assessing processor 560, the image correcting processor 570, and the analyzing processor 580. The part image assessing processor 550 includes the assessment region setting processor 551 and the assessment data generating processor 552. The analyzing processor 580 may include the corner angle analyzing processor 581. Each of these elements may have the same (or similar) configuration and the same (or similar) function as (or to) a corresponding element in the ophthalmic apparatus 1 described above (see, for example, FIG. 4).

An example of the operation of the ophthalmic apparatus 500 will now be described with referring again to FIG. 10. To begin with, the ophthalmic apparatus 500 acquires an anterior segment image of the subject's eye E by the image receiver 530 (S1). Then, the part image identifying processor 540 identifies two or more part images respectively corresponding to two or more parts of the anterior segment Ea, from the anterior segment image acquired in the step S1 (S2). Next, the assessment region setting processor 551 of the part image assessing processor 550 sets an assessment region for image quality assessment, for each part image identified in the step S2 (S3). Next, for each part image identified in the step S2, the assessment data generating processor 552 of the part image assessing processor 550 generates assessment data of that part image by analyzing a corresponding assessment region set for that part image in the step S3 (S4). Next, the anterior segment image assessing processor 560 assesses the image quality of the anterior segment image acquired in the step S1, based on the two or more pieces of assessment data obtained for the two or more part images in the step S4 (S5).

If the image quality of the anterior segment image is assessed to be satisfactory in the step S5 (S6: Yes), the process moves on to the step S7. On the other hand, if the image quality of the anterior segment image is assessed to be unsatisfactory in the step S5 (S6: No), the process moves back to the step S1 and the series of processes of the steps S1 to S5 is repeated until a predetermined condition is satisfied.

An example of processing executed when a judgement result "No" is obtained in the step S6, will now be described. Suppose that an ophthalmic OCT apparatus (not shown in the drawings) is connected to the ophthalmic apparatus 500 in a direct or indirect fashion. In other words, suppose that data communication is established between the ophthalmic apparatus 500 and the ophthalmic OCT apparatus. If the image quality of the anterior segment image is assessed to be unsatisfactory by the anterior segment image assessing processor 560 (S6: No), the controller 510 may send a request signal for re-application of OCT scanning to the anterior segment Ea of the subject's eye E, to the ophthalmic OCT apparatus. This makes it possible to automatically request the ophthalmic OCT apparatus to acquire another anterior segment image (new anterior segment image) of the anterior segment Ea in the case in which an anterior segment image with an unsatisfactory image quality is acquired. Note that a destination (recipient) of the request signal is not limited to the ophthalmic OCT apparatus, but may be an operator (user) of the ophthalmic OCT apparatus or the like.

If the image quality is assessed to be satisfactory in the step S6 (S6: Yes), the image correcting processor 570 applies a predetermined correction processing to the anterior segment image (S7). Next, the corner angle analyzing processor 581 of the analyzing processor 580 executes calculation of a predetermined corner angle parameter by analyzing the anterior segment image obtained by the step S7 (S8). The controller 510 controls the user interface 520 to display, for example, the anterior segment image obtained by the step S7 and information on the corner angle parameter obtained in the step S8 (S9). Further, the controller 510 saves an anterior segment image of the subject's eye E and the information on the corner angle parameter obtained in the step S8 in a predetermined storage device (S10). This completes the present operation example (End).

<Actions and Effects>

Some features, some actions, and some advantageous effects of some aspect examples of embodiments will now be described.

An ophthalmic apparatus (1; 500) according to some aspect examples includes an image acquiring unit (2, 100, 220; 530), a part image identifying processor (231; 540), a part image assessing processor (232; 550), and an anterior segment image assessing processor (233; 560). The image acquiring unit is configured to acquire an anterior segment image constructed based on data collected from an anterior segment (Ea) of a subject's eye (E) by optical coherence tomography (OCT) scanning. The part image identifying processor is configured to identify two or more part images respectively corresponding to two or more parts of the anterior segment, from the anterior segment image acquired by the image acquiring unit. The part image assessing processor is configured to assess image quality of each of the two or more part images identified from the anterior segment image by the part image identifying processor. The anterior segment image assessing processor is configured to assess image quality of the anterior segment image based on two or more pieces of assessment data respectively obtained for the two or more part images by the part image assessing processor.

In some aspect examples, the part image assessing processor (232; 550) may include an assessment region setting processor (2321; 551) and an assessment data generating processor (2322; 552). The assessment region setting processor is configured to set an assessment region for each of the two or more part images identified from the anterior segment image by the part image identifying processor. The assessment data generating processor is configured to generate assessment data of the image quality of a part image by analyzing a corresponding assessment region set for this part image by the assessment region setting processor.

In some aspect examples, the assessment region setting processor (2321; 551) may further be configured to set an assessment region for each of the two or more part images identified from the anterior segment image by the part image identifying processor, in such a manner that this assessment region includes a first region and a second region. Here, the first region is at least part of a corresponding part image, and the second region is located outside the corresponding part image.

In some aspect examples, the assessment region setting processor (2321; 551) may further be configured to set the assessment region in such a manner that the first region and the second region are adjacent to each other.

In some aspect examples, the part image identifying processor (231; 540) may further be configured to identify a first part image group if the anterior segment image acquired by the image acquiring unit (2, 100, 220; 530) is a wide angle image, and to identify a second part image group, which is different from the first part image group, if the anterior segment image by the image acquiring unit is a non-wide angle image.

In some aspect examples, the number of part images included in the first part image group identified from the wide angle image and the number of part images included in the second part image group identified from the non-wide angle image may be different from each other.

In some aspect examples, the part image identifying processor (231; 540) may further be configured to identify a part image by applying edge detection to the anterior segment image acquired by the image acquiring unit (2, 100, 220; 530).

In some aspect examples, the part image identifying processor (231; 540) may further be configured to identify a cornea image and an iris image from the anterior segment image acquired by the image acquiring unit (2, 100, 220; 530). Also, the part image assessing processor (232; 550) may further be configured to assess image quality of the cornea image and assess image quality of the iris image. In addition, the anterior segment image assessing processor (233; 560) may further be configured to assess image quality of the anterior segment image based on assessment data obtained for the cornea image and assessment data obtained for the iris image.

In some aspect examples, the part image assessing processor (232; 550) may include an assessment region setting processor (2321; 551) and an assessment data generating processor (2322; 552). The assessment region setting processor is configured to set a cornea assessment region for the cornea image, and to set an iris assessment region for the iris image. The assessment data generating processor is configured to generate cornea assessment data by analyzing the cornea assessment region, and to generate iris assessment data by analyzing the iris assessment region.

In some aspect examples, the assessment region setting processor (2321; 551) may further be configured to set the cornea assessment region in such a manner that the cornea assessment region includes an intra-cornea region and an extra-cornea region. Here, the intra-cornea region is at least part of the cornea image, and the extra-cornea region is located outside the cornea image. In addition, the assessment region setting processor may further be configured to set the iris assessment region in such a manner that the iris assessment region includes an intra-iris region and an extra-iris region. Here, the intra-iris region is at least part of the iris image, and the extra-iris region is located outside the iris image.

In some aspect examples, the assessment region setting processor (2321; 551) may further be configured to set the cornea assessment region in such a manner that the intra-cornea region and the extra-cornea region are adjacent to each other, and to set the iris assessment region in such a manner that the intra-iris region and the extra-iris region are adjacent to each other.

In some aspect examples, the part image identifying processor (231; 540) may further be configured to identify the cornea image by identifying a first cornea image and a second cornea image, and to identify the iris image by identifying a first iris image and a second iris image, if the anterior segment image acquired by the image acquiring unit (2, 100, 220: 530) is a wide angle image. Here, the first cornea image is located in a vicinity of a first frame edge of the anterior segment image, the second cornea image is located in a vicinity of a second frame edge opposite to the first frame edge, the first iris image is located in a vicinity of the first frame edge, and the second iris image is located in a vicinity of the second frame edge. In addition, the part image identifying processor may further be configured to identify the cornea image by identifying a single cornea image from the anterior segment image acquired by the image acquiring unit, and to identify the iris image by identifying a single iris image from this anterior segment image, if this anterior segment image is a non-wide angle image.

In some aspect examples, the part image identifying processor (231; 540) may further be configured to identify the cornea image and the iris image by applying edge detection to the anterior segment image acquired by the image acquiring unit (2, 100, 220: 530).

In some aspect examples, the part image identifying processor (231; 540) may further be configured to identify either one or both of an anterior corneal surface image and a posterior corneal surface image by the edge detection, and to identify an anterior iridic surface image by the edge detection. Moreover, the part image identifying processor may further be configured to identify the cornea image based on the anterior corneal surface image and/or the posterior corneal surface image identified. In addition, the part image identifying processor may further be configured to identify the iris image based on the anterior iridic surface image identified.

In some aspect examples, the part image identifying processor (231; 540) may further be configured to identify the anterior corneal surface image by identifying an edge where a gradient direction is toward a frame edge of the anterior segment image and where a gradient value is equal to or greater than a predetermined threshold value.

In some aspect examples, the part image identifying processor (231; 540) may further be configured to identify the posterior corneal surface image by identifying an edge where a gradient direction is toward a central region of a frame of the anterior segment image and where a gradient value is equal to or greater than a predetermined threshold value.

The ophthalmic apparatus (1; 500) of some aspect examples may further include an image correcting processor (234; 570) configured to correct a pixel aspect ratio of the anterior segment image.

In some aspect examples, the image correcting processor (234; 570) may further be configured to correct the pixel aspect ratio of the anterior segment image with an image quality assessed to be satisfactory by the anterior segment image assessing processor (233; 560).

The ophthalmic apparatus (1; 500) of some aspect examples may further include a corner angle analyzing processor (2351; 581) configured to calculate a predetermined corner angle parameter by analyzing the anterior segment image whose pixel aspect ratio has been corrected by the image correcting processor (234; 570).

In some aspect examples, the anterior segment image assessing processor (233; 560) may further be configured to assess the image quality of the anterior segment image by applying a predetermined statistical calculation to the two or more pieces of assessment data obtained for the two or more part images by the part image assessing processor (232; 550).

In some aspect examples, the anterior segment image assessing processor (233; 560) may further be configured to assess the image quality of the anterior segment image by applying at least an averaging calculation to the two or more pieces of assessment data obtained for the two or more part images by the part image assessing processor (232; 550).

In some aspect examples, the anterior segment image assessing processor (233; 560) may further be configured to assess the image quality of the anterior segment image by performing at least selection of assessment data corresponding to a lowest image quality by comparing the two or more pieces of assessment data obtained for the two or more part images by the part image assessing processor (232; 550).

The ophthalmic apparatus (1; 500) of some aspect examples may further include an analyzing processor (235; 580) configured to calculate a predetermined anterior segment parameter by analyzing the anterior segment image acquired by the image acquiring unit (2, 100, 220; 530).

In some aspect examples, the image acquiring unit (2, 100, 220) may include a data collector (2, 100) configured to collect data by applying OCT scanning to the anterior segment, and an image constructing processor (220) configured to construct an anterior segment image based on the data collected by the data collector.

In some aspect examples, the data collector (2, 100) may be configured to collect another data (new data) by applying OCT scanning to the anterior segment again if the image quality of the anterior segment image is assessed to be unsatisfactory by the anterior segment image assessing processor. In addition, the image constructing processor (220) may be configured to construct another anterior segment image (new anterior segment image) based on the new data collected by the data collector.

In some aspect examples, the image acquiring unit (530) may include a receiver (530) that receives the anterior segment image from an outside source.

The ophthalmic apparatus (500) of some aspect examples may further include a signal output unit (the controller 510) configured to output a signal representing a need for re-application of OCT scanning to the subject's eye if the image quality of the anterior segment image is assessed to be unsatisfactory by the anterior segment image assessing processor (560).

The ophthalmic apparatus (1; 500) of the aspect examples is configured to perform assessment of the image quality of an anterior segment image based on a plurality of pieces of assessment data obtained by assessing the image qualities of a plurality of part images of this anterior segment image. With this configuration, the ophthalmic apparatus of the aspect examples is capable of determining, for example, whether both cornea and iris are depicted with satisfactory image quality, thereby contributing to accurate determination of a corner angle position. As a result, according to the ophthalmic apparatus (1; 500) of the aspect examples, various advantageous effects can be achieved such as the improvement of the quality of corner angle analysis, avoidance of redoing of OCT scanning, and avoidance of lengthening of examination.

It should be noted that the ophthalmic apparatus (1; 500) of the aspect examples may also be applicable to any purposes other than corner angle analysis. More generally, the ophthalmic apparatus (1; 500) of the aspect examples may be used for anterior segment analysis in which detection of two or more parts of an anterior segment is required. With this, in various kinds of anterior segment analysis such as anterior chamber depth analysis for obtaining the distance between cornea and iris, various advantageous effects can be achieved such as the improvement of the quality of analysis, avoidance of redoing of OCT scanning, and avoidance of lengthening of examination.

As described above, the ophthalmic apparatus (1; 500) of the aspect examples is capable of making an improvement in OCT anterior segment analysis.

Some aspect examples provide a method of controlling an ophthalmic apparatus. The ophthalmic apparatus to which this control method is applied includes at least a processor. This control method includes the first control step, the second control step, and the third control step.

The first control step controls the processor to perform identification of two or more part images respectively corresponding to two or more parts of an anterior segment of a subject's eye from an anterior segment image constructed based on data collected from the anterior segment by optical coherence tomography (OCT) scanning. The second control step controls the processor to perform image quality assessment of each of the two or more part images identified. The third control step controls the processor to perform image quality assessment of the anterior segment image based on two or more pieces of assessment data respectively obtained for the two or more part images identified.

Any matters and items of the aspect examples described above may be incorporated with this method of controlling an ophthalmic apparatus.

Some aspect examples provide a program configured to cause a computer (ophthalmic apparatus) to execute the method of controlling an ophthalmic apparatus. Any matters and items of the aspect examples described above may be incorporated with this program.

Some aspect examples provide a computer-readable non-transitory recording medium that retains this program. Any matters and items of the aspect examples described above may be incorporated with this recording medium. This recording medium may be in any form. Examples of this recording medium include a magnetic disk, an optical disk, a magneto-optical disk, a semiconductor memory, and any other kinds of recording media.

As with the ophthalmic apparatus (1; 500) of the aspect examples, the control method, the program, or the recording medium of the aspect examples is capable of making an improvement in OCT anterior segment analysis. Further, the control method, the program, or the recording medium of the aspect examples is capable of achieving additional actions and additional advantageous effects corresponding to matters and items optionally incorporated.

The aspect examples disclosed herein are merely some non-limiting examples of embodiments of the present invention, and any modifications (e.g., omissions, substitutions, replacements, additions, etc.) can be made within the scope of the gist of the present invention.

What is claimed is:

1. An ophthalmic apparatus comprising:
   an image acquiring unit configured to acquire an anterior segment image constructed based on data collected from an anterior segment of a subject's eye by optical coherence tomography (OCT) scanning;

a part image identifying processor configured to perform identification of a cornea image and identification of an iris image from the anterior segment image acquired by the image acquiring unit;

a part image assessing processor configured to perform image quality assessment of the cornea image to generate cornea assessment data and image quality assessment of the iris image to generate iris assessment data;

an anterior segment image assessing processor configured to perform image quality assessment of the anterior segment image by applying a predetermined statistical calculation to the cornea assessment data and the iris assessment data to derive a statistic and by determining whether the statistic satisfies a predetermined condition;

an image correcting processor configured to perform correction of a pixel aspect ratio of the anterior segment image only under a condition that the statistic is determined to satisfy the predetermined condition by the anterior segment image assessing processor;

a corner angle analyzing processor configured to perform calculation of a predetermined corner angle parameter by analyzing the anterior segment image whose pixel aspect ratio has been corrected by the image correcting processor;

a display device; and a controller configured to display the anterior segment image with the pixel aspect ratio corrected on the display device and display a measurement position and a measured value of the predetermined corner angle parameter over the anterior segment image displayed on the display device.

2. The ophthalmic apparatus of claim 1, wherein the part image assessing processor includes:

an assessment region setting processor configured to perform setting of a cornea assessment region for the cornea image, and to perform setting of an iris assessment region for the iris image; and an assessment data generating processor configured to perform generation of the cornea assessment data by analyzing the cornea assessment region, and to perform generation of the iris assessment data by analyzing the iris assessment region.

3. The ophthalmic apparatus of claim 2, wherein the assessment region setting processor is further configured to perform the setting of the cornea assessment region in such a manner that the cornea assessment region includes an intra- cornea region and an extra-cornea region, the intra-cornea region being at least part of the cornea image and the extra-cornea region being located outside the cornea image, and the assessment region setting processor is further configured to perform the setting of the iris assessment region in such a manner that the iris assessment region includes an intra-iris region and an extra-iris region, the intra-iris region being at least part of the iris image and the extra-iris region being located outside the iris image.

4. The ophthalmic apparatus of claim 3, wherein the assessment region setting processor is further configured to perform the setting of the cornea assessment region in such a manner that the intra-cornea region and the extra-cornea region are adjacent to each other, and the assessment region setting processor is further configured to perform the setting of the iris assessment region in such a manner that the intra-iris region and the extra-iris region are adjacent to each other.

5. The ophthalmic apparatus of claim 1, wherein the part image identifying processor is further configured to perform the identification of the cornea image by identifying a first cornea image and a second cornea image, the first cornea image being located in a vicinity of a first frame edge of the anterior segment image and the second cornea image being located in a vicinity of a second frame edge opposite to the first frame edge, and to perform the identification of the iris image by identifying a first iris image and a second iris image, the first iris image being located in a vicinity of the first frame edge and the second iris image being located in a vicinity of the second frame edge, if the anterior segment image acquired by the image acquiring unit is a wide angle image, and the part image identifying processor is further configured to perform the identification of the cornea image by identifying a single cornea image, and to perform the identification of the iris image by identifying a single iris image, if the anterior segment image is a non-wide angle image.

6. The ophthalmic apparatus of claim 1, wherein the part image identifying processor is further configured to perform the identification of the cornea image and the identification of the iris image by applying edge detection to the anterior segment image acquired by the image acquiring unit.

7. The ophthalmic apparatus of claim 6, wherein the part image identifying processor is further configured to perform identification of one or both of an anterior corneal surface image and a posterior corneal surface image and identification of an anterior iridic surface image by the edge detection, the part image identifying processor is further configured to perform the identification of the cornea image based on the one or both of the anterior corneal surface image and the posterior corneal surface image, and the part image identifying processor is further configured to perform the identification of the iris image based on the anterior iridic surface image.

8. The ophthalmic apparatus of claim 7, wherein the part image identifying processor is further configured to perform the identification of the anterior corneal surface image by identifying an edge where a gradient direction is toward a frame edge of the anterior segment image and where a gradient value is equal to or greater than a predetermined threshold value.

9. The ophthalmic apparatus of claim 7, wherein the part image identifying processor is further configured to perform the identification of the posterior corneal surface image by identifying an edge where a gradient direction is toward a central region of a frame of the anterior segment image and where a gradient value is equal to or greater than a predetermined threshold value.

* * * * *